US012653919B2

(12) United States Patent (10) Patent No.: US 12,653,919 B2
Inoue et al. (45) Date of Patent: Jun. 16, 2026

(54) PERFUME RETAINING MEMBER AND SCENT PROVIDING DEVICE

(71) Applicant: Sony Group Corporation, Tokyo (JP)

(72) Inventors: Yukito Inoue, Tokyo (JP); Shuji Fujita, Tokyo (JP); Shinya Ootani, Tokyo (JP)

(73) Assignee: Sony Group Corporation, Tokyo (JP)

( * ) Notice: Subject to any disclaimer, the term of this patent is extended or adjusted under 35 U.S.C. 154(b) by 250 days.

(21) Appl. No.: 18/285,725

(22) PCT Filed: Mar. 17, 2022

(86) PCT No.: PCT/JP2022/012379
§ 371 (c)(1),
(2) Date: Oct. 5, 2023

(87) PCT Pub. No.: WO2022/220011
PCT Pub. Date: Oct. 20, 2022

(65) Prior Publication Data
US 2024/0197945 A1 Jun. 20, 2024

(30) Foreign Application Priority Data

Apr. 16, 2021 (JP) ................................. 2021-069691

(51) Int. Cl.
*A61L 9/12* (2006.01)
(52) U.S. Cl.
CPC ........... *A61L 9/12* (2013.01); *A61L 2209/133* (2013.01)
(58) Field of Classification Search
CPC .............................. A61L 9/12; A61L 2209/133
(Continued)

(56) References Cited

U.S. PATENT DOCUMENTS 8,523,020 B2 * 9/2013 Abfall ................. B05B 11/0038
239/57
2002/0179727 A1 12/2002 Paul, Jr.

FOREIGN PATENT DOCUMENTS

CN 1314295 A 9/2001
CN 211033630 U 7/2020
(Continued)

OTHER PUBLICATIONS

International Search Report and English translation thereof mailed May 31, 2022 in connection with International Application No. PCT/JP2022/012379.
(Continued)

*Primary Examiner* — Christopher S Kim
(74) *Attorney, Agent, or Firm* — Wolf, Greenfield & Sacks, P.C.

(57) ABSTRACT

Provided is a perfume retaining member which is easy to handle and in which perfume can be stored for a long period of time without leakage.
The perfume retaining member 101 includes: a housing 111 that includes an internal space, a first opening 117 and a second opening 118 that open the internal space to an outside, and movable portions 113 and 114 that are movable to open and close at least one of the first opening 117 or the second opening 118; a perfume storage unit 120 that stores perfume in a sealed manner; a perfume releasing mechanism 124 that releases the perfume from the perfume storage unit 120; and an impregnating material 115 in which the perfume released from the perfume storage unit 120 impregnates to be retained. The movable portions 113 and 114 seal the first opening 117 and/or the second opening 118 in a fixed time, and open the first opening 117 and/or the second opening 118 when the internal space is opened.

18 Claims, 14 Drawing Sheets

(58) Field of Classification Search
USPC ............................................. 239/53, 55, 56
See application file for complete search history.

(56) References Cited

FOREIGN PATENT DOCUMENTS

| | | | |
|---|---|---|---|
| DE | 102018008082 | A | 4/2020 |
| JP | H09-000421 | U | 7/1997 |
| JP | 2007-276831 | A | 10/2007 |
| JP | 2011-083453 | A | 4/2011 |
| JP | 2013-094436 | A | 5/2013 |
| JP | 2014-108211 | A | 6/2014 |
| JP | 2016073464 | A | 5/2016 |
| JP | 2016-522701 | A | 8/2016 |
| WO | WO 2014/176291 | A1 | 10/2014 |
| WO | WO-2016164917 | A1 | 10/2016 |
| WO | WO-2019066100 | A1 | 4/2019 |
| WO | WO 2020/026662 | A1 | 2/2020 |
| WO | WO-2022184241 | A1 | 9/2022 |

OTHER PUBLICATIONS

International Written Opinion and English translation thereof mailed May 31, 2022 in connection with International Application No. PCT/JP2022/012379.

International Preliminary Report on Patentability and English translation thereof mailed Oct. 26, 2023 in connection with International Application No. PCT/JP2022/012379.

Extended European Search Report issued Sep. 23, 2024 in connection with European Application No. 22787937.6.

* cited by examiner

A                                    B

A                 B

A                                    B

A                                    B

A

B

A                    B

A                    B

A                    B

A　　　　　　　　　　B

A                    B                    C

A                    B

PERFUME RETAINING MEMBER AND SCENT PROVIDING DEVICE

CROSS-REFERENCE TO RELATED APPLICATIONS

The present application claims the benefit under 35 U.S.C. § 371 as a U.S. National Stage Entry of International Application No. PCT/JP2022/012379, filed in the Japanese Patent Office as a Receiving Office on Mar. 17, 2022, which claims priority to Japanese Patent Application Number JP2021-069691, filed in the Japanese Patent Office on Apr. 16, 2021, each of which applications is hereby incorporated by reference in its entirety.

TECHNICAL FIELD

The present technology relates to a perfume retaining member and a scent providing device, and more particularly to a perfume retaining member and a scent providing device that provides scent with perfume retained inside by opening and closing an air supply path and a scent release path.

BACKGROUND ART

Conventionally, there has been proposed a technique of supplying air to a storage device in which a perfume retaining member retaining perfume is stored and releasing vaporized perfume with air flow to provide scent to a user.

For example, Patent Document 1 proposes a scent providing device including: a cylindrical shield tube whose inner hollow is used as a fragrance transporting passage and which has an opening on a part of a side surface; a fragrance container in which the fragrance is stored, which is provided on the outer surface of the shield tube and which has an opening on a side surface on the shield tube side; and a blower means disposed at one end of the fragrance transporting passage for blowing air. The interior of the fragrance container and the fragrance transporting passage can be brought into a penetrating state when the opening of the shield tube and the opening of the fragrance container are overlapped by relative rotational motions of the shield tube and the fragrance container while the shield tube and the fragrance container are closely attached to each other, and the interior of the fragrance container and the fragrance transporting passage can be brought into a non-penetrating state when the opening of one of the shield tube and the fragrance container are overlapped with a portion other the opening of the one by relative rotational motions of the shield tube and the fragrance container while the shield tube and the fragrance container are closely attached to each other.

According to the scent providing device described in Patent Document 1, unintended release of perfume can be suppressed, and scent can be provided at an appropriate timing.

CITATION LIST

Patent Document

Patent Document 1: Japanese Patent Application Laid-Open No. 2013-094436

SUMMARY OF THE INVENTION

Problems to be Solved by the Invention

However, in the scent providing device of Patent Document 1, when a long period of time elapses before the perfume retaining member is used, the perfume may deteriorate (weakening due to volatilization and degeneration due to oxidation), and handling may be inconvenient. Furthermore, there is a concern that leakage of perfume from a fitting portion between a container retaining perfume and a case or an opening such as a scent entrance for communicating with the outside may cause a problem such as odor transfer during assembly.

In this regard, a main object of the present technology is to provide a perfume retaining member which is easy to handle and in which perfume can be stored for a long period of time without leakage.

Solutions to Problems

According to the present technology, a perfume retaining member is provided which includes: a housing that includes an internal space, a first opening and a second opening that open the internal space to an outside, and a movable portion that is movable to open and close at least one of the first opening or the second opening; a perfume storage unit that stores perfume in a sealed manner; a perfume releasing mechanism that releases the perfume from the perfume storage unit; and a perfume retainer in which the perfume released from the perfume storage unit impregnates to be retained. The movable portion seals the first opening and/or the second opening in a fixed time, and opens the first opening and/or the second opening when the internal space is opened.

Furthermore, according to the present technology, a scent providing device is provided which includes: a perfume retaining member including a housing that includes an internal space, a first opening and a second opening that open the internal space to an outside, and a movable portion that is movable to open and close at least one of the first opening or the second opening, a perfume storage unit that stores perfume in a sealed manner, a perfume releasing mechanism that releases the perfume from the perfume storage unit, and a perfume retainer in which the perfume released from the perfume storage unit impregnates to be retained; and a drive mechanism portion that is connected to the movable portion and drives the movable portion. The movable portion seals the first opening and/or the second opening in a fixed time, and opens the first opening and/or the second opening when the internal space is opened.

Effects of the Invention

According to the present technology, it is possible to provide a perfume retaining member which is easy to handle and in which perfume can be stored for a long period of time without leakage. Note that effects described above are not necessarily limited, and any of the effects described in the present specification or other effects that can be grasped from the present specification may be exhibited in addition to or in place of the effects described above.

MODE FOR CARRYING OUT THE INVENTION

Hereinafter, preferred modes for carrying out the present technology will be described with reference to the drawings. Embodiments to be described hereinafter illustrate examples of representative embodiments of the present technology, and any embodiments can be combined. Furthermore, the scope of the present technology is not narrowly construed based on these. Note that description will be given in the following order.

Figure 1:
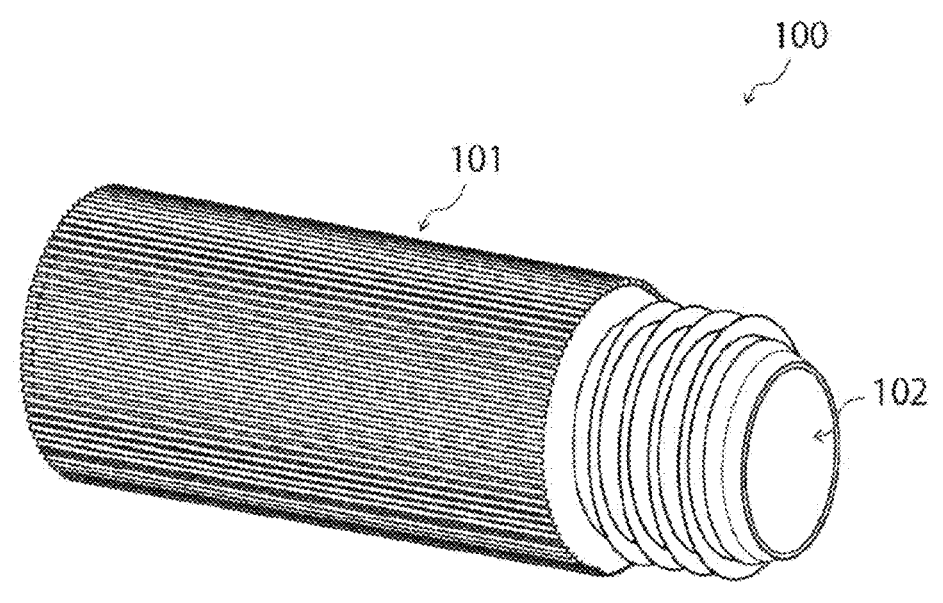
FIG. 1 is a perspective view illustrating a configuration example of a scent providing device according to a first embodiment of the present technology.
Figure 2:
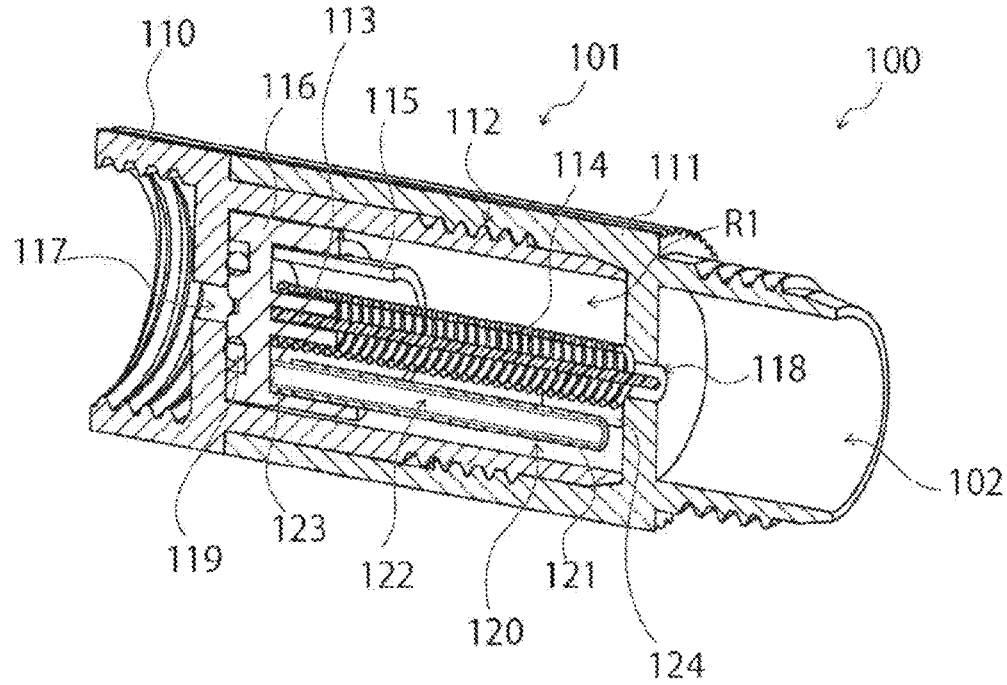
FIG. 2 is a cross-sectional perspective view illustrating a configuration example of a perfume retaining member according to the first embodiment of the present technology.

1. First Embodiment
(1) Configuration Example of Scent Providing Device
(1-1) Overall Configuration
(1-2) Perfume Cartridge (Perfume Retaining Member)
(1-3) Drive Mechanism Portion
(2) Operation Example of Scent Providing Device
(3) Modification of Perfume Storage Unit
2. Second Embodiment
(1) Configuration Example of Scent Providing Device
(2) Operation Example of Scent Providing Device
3. Third Embodiment
(1) Configuration Example of Scent Providing Device
(2) Operation Example of Scent Providing Device
4. Fourth Embodiment
(1) Configuration Example of Scent Providing Device
(2) Operation Example of Scent Providing Device
5. Fifth Embodiment
(1) Configuration Example of Scent Providing Device
(2) Operation Example of Scent Providing Device
6. Sixth Embodiment
(1) Configuration Example of Perfume Cartridge
(2) Operation Example of Perfume Cartridge
7. Seventh Embodiment
8. Eighth Embodiment
(1) Configuration Example of Perfume Cartridge
(2) Operation Example of Perfume Cartridge
9. Ninth Embodiment
(1) Configuration Example of Scent Providing Device
(2) Operation Example of Scent Providing Device
10. Tenth Embodiment
(1) Configuration Example of Scent Providing Unit
(2) Operation example of Scent Providing Unit
11. Eleventh Embodiment
12. Twelfth Embodiment
13. Thirteenth Embodiment 1. First Embodiment (1) Configuration Example of Scent Providing Device
(1-1) Overall Configuration
Next, a configuration example of a scent providing device 100 according to a first embodiment of the present technology will be described with reference to FIGS. 1 and 2. FIG. 1 is a perspective view illustrating the configuration example of the scent providing device 100 according to the present embodiment. FIG. 2 is a cross-sectional perspective view illustrating a configuration example of a perfume cartridge (perfume retaining member) 101 included in the scent providing device 100.

As illustrated in FIG. 1, the scent providing device 100 according to the present embodiment includes a cylindrical perfume cartridge 101 that is a perfume retaining member, a cylindrical drive mechanism portion (not illustrated), and a discharge hole 102 that is formed at the distal end of the perfume cartridge 101 and releases flavored air containing perfume to the outside.

As illustrated in FIG. 2, the scent providing device 100 is a device that allows air to flow into an internal space R1 provided in the perfume cartridge 101, and vaporizes and releases the perfume retained in a perfume retainer 115 arranged in the internal space R1. For example, in the scent providing device 100, the perfume retainer 115 is arranged in the internal space R1 of a housing 111 of the perfume cartridge 101, and air supplied from an air pump (not illustrated) is caused to flow to vaporize liquid perfume or moist perfume (hereinafter, referred to as liquid perfume), so that scent is released together with the air from the internal space R1 to the outside through the discharge hole 102.

The scent providing device 100 is used, for example, as a device that releases scent into a limited range of space. For example, a user releases scent from the scent providing device 100 once or a plurality of times near his/her face to relax his/her mood. In this case, since the scent providing device 100 releases the scent with high straightness and makes it difficult to diffuse the scent over a wide range, it is possible to make it difficult for surrounding people to sense the scent. The scent providing device 100 may be a portable device that can be carried by the user, or may be a stationary device.

(1-2) Perfume Cartridge (Perfume Retaining Member)

Next, a configuration example of the perfume cartridge 101 as the perfume retaining member included in the scent providing device 100 according to the present embodiment will be described.

As illustrated in FIG. 2, the perfume cartridge 101 includes a connection unit 110 detachably connected to the drive mechanism portion, and a housing 111 connected to the connection unit 110. The perfume cartridge 101 has a cylindrical shape, but the outer shape of the perfume retaining member according to the present technology is not limited to the cylindrical shape, and may be, for example, a column, a rectangular parallelepiped, a cube, or any other appropriate shape.

The connection unit 110 is connected in a sealed manner by being screwed with the housing 111 by a threaded portion 112. The connection unit 110 includes an operation shaft therein. In the perfume cartridge 101, the fitting portion with the connection unit 110 can be sealed by the threaded portion 112 to prevent perfume leakage from the fitting portion. Furthermore, an O-ring can be arranged at the fitting portion between the connection unit 110 and the threaded portion 112 to seal the fitting portion. Note that it is sufficient if the O-ring has a sealed structure with high airtightness capable of sealing the fitting portion, and the O-ring may have a fitting structure of a protrusion or the like. Furthermore, the fitting portion may include an oil seal material and/or an elastic material.

The housing 111 includes an internal space R1, a first opening 117 and a second opening 118 that open the internal space R1 to the outside and release flavored air, in which perfume and air are mixed, toward the discharge hole 102, and a first shaft 113 as an operation shaft and a first spring 114 as an elastic body, the first shaft 113 and the first spring 114 being movable portions which are movable to open and close the first opening 117. The housing 111 includes a material such as a polymer resin, metal, inorganic crystal, or glass having low gas permeability in order to seal the perfume so as not to leak to the outside. Note that the first shaft 113 and the first spring 114 may be movable portions which are movable to open and close at least one of the first opening 117 or the second opening 118.

The first shaft 113 is arranged across the central portion of the internal space R1, and the first spring 114 is arranged to surround the periphery of the first shaft 113. A first sealing valve 116 that seals the first opening 117 is connected to the end portion of the first shaft 113 on the first opening 117 side.

The first spring 114 biases the first sealing valve 116 in a direction of sealing the first opening 117. However, the first spring 114 may be biased in the sealing direction of the first opening 117 and/or the second opening 118. Note that although a coil spring is used as an example, the first spring 114 is not limited thereto, and may be a leaf spring or the like as long as the first spring 114 is an elastic body capable of biasing the first sealing valve 116 in the sealing direction of the first opening 117.

Moreover, in the vicinity of the first sealing valve 116 in the internal space R1, the perfume retainer 115 such as an impregnating material retaining liquid perfume is arranged to surround the periphery of the first spring 114. As described above, by arranging the perfume retainer 115 outside the first spring 114, the wind passing through the internal space R1 easily hits the perfume retainer 115, and the discharge amount of the perfume can be increased.

The perfume retainer 115 retains liquid perfume. The perfume retainer 115 has a cylindrical shape that covers and surrounds the side surface of the operation shaft, but may have a rod shape, a plate shape, a prismatic shape with a hollow inside, or the like. The liquid perfume may be, for example, an essential oil or an essential oil diluted with ethanol. The internal space R1 serves as a ventilation path through which air supplied from an air pump (not illustrated) which is an example of a blowing source passes. Each of the internal spaces R1 may be one space or may be divided into a plurality of spaces.

Liquid perfume is attached to and retained in a wet state in at least a part of the inner surface of the internal space R1. For example, after the internal space R1 is filled with the liquid perfume, a high pressure gas such as air is supplied into the internal space R1 for a predetermined time, so that excess liquid perfume can be ejected, and the perfume can be attached in a wet state to the inner surface of the internal space R1.

The perfume retainer 115 may include an organic polymer material so that the liquid perfume is likely to infiltrate. As the organic polymer material, for example, any one of polyvinyl chloride, polyethylene, a phenol resin, an olefin resin, nylon, polyester, a synthetic rubber, a silicone resin, a natural rubber, a protein, a nucleic acid, a lipid, or a polysaccharide, or a mixture thereof can be used. However, the perfume retainer 115 is not limited to these examples. For example, a polymer resin such as an acrylic resin, a urethane resin, an ABS resin, a polyether ether ketone (PEEK) resin, a polyacetal (POM) resin, a fluororesin, a cycloolefin polymer resin, or a polyimide resin, or one or more types of materials of a metal such as stainless steel or aluminum, an inorganic crystal such as quartz, or glass may be used. Moreover, the perfume retainer 115 may be formed to be porous. As the porous material, a mesh structure, cork, mesoporous silica, calcium carbonate, or the like can be used. Furthermore, as the perfume retainer 115, a fiber structure, a layered structure (clay mineral or the like), ceramic, or the like can also be used other than the porous material. Furthermore, the surface of the perfume cartridge 101 may include a material selected from any one of a low-gas-permeable resin, an organic polymer, an organic low molecule, an organic metal, a metal, or a metal film, or a combination of a plurality of these.

In the first sealing valve 116, as an example for enhancing sealing force, an O-ring 119 is attached to a contact surface with a wall surface in which the first opening 117 is formed inside the housing 111. Furthermore, a perfume storage unit (ampule cartridge) 120 that stores perfume in a sealed manner is provided on the surface side of the first sealing valve 116 facing a contact surface with the housing 111.

As an example, the perfume storage unit 120 is formed in a cylindrical shape extending in a direction parallel to the first shaft 113, which is a movable direction of the movable portion, and has one end fixed to the first sealing valve 116. The perfume storage unit 120 has a surface covered with a heat-shrinkable tube 121 that is a protective member covering the periphery of the perfume storage unit 120, and includes a glass pipe 122 that stores perfume therein. The heat-shrinkable tube 121 can include an elastic body. The material of the perfume storage unit 120 may be any material as long as the material has low gas permeability and can seal the perfume, and may be metal or the like.

The perfume storage unit 120 is arranged to be adjacent to the perfume retainer 115. A part of the glass pipe 122 in the vicinity of the perfume retainer 115 is an exposed portion 123 that is exposed without being covered with the heat-shrinkable tube 121. Therefore, the perfume released from the perfume storage unit 120 can be smoothly guided to the perfume retainer 115. Note that the perfume storage unit 120 can also be arranged in the movable portion.

On the wall surface in which the second opening 118 is formed inside the housing 111, a perfume releasing mechanism 124 is provided at a position which is brought into contact with the other end of the perfume storage unit 120 when the housing 111 is rotated in a direction perpendicular to the extending direction thereof. As an example, the perfume releasing mechanism 124 has a columnar shape, but the shape is not limited thereto. In the perfume cartridge 101, when the housing 111 is rotated and screwed into the connection unit 110, the other end of the perfume storage unit 120 can be pushed down by the perfume releasing mechanism 124 to split the glass pipe 122 of the perfume storage unit 120. Therefore, the perfume stored in the glass pipe 122 can be released to the outside to be permeated into the perfume retainer 115 from the exposed portion 123.

The operation shaft inside the connection unit 110 is movable in an extending direction from the inside of the connection unit 110 toward the internal space R1. The first shaft 113 is connected via the first sealing valve 116 to the distal end of the operation shaft in the direction of the discharge hole 102, and is movable in the extending direction of the internal space R1 together with the operation shaft. Note that the operation shaft and the first shaft 113 can be a linear motion mechanism that linearly moves in the opening/closing direction of the first opening 117 and the second opening 118.

The first shaft 113 is a movable portion which is movable to open and close the first opening 117 by the first sealing valve 116, and in a fixed time, the first sealing valve 116 is brought into contact with the first opening 117 by the first spring 114 to be sealed. Therefore, the perfume cartridge 101 can prevent perfume leakage from the first opening 117. Note that the movable portion according to the present technology can seal the first opening 117 and/or the second opening 118 in the fixed time, and can open the first opening 117 and/or the second opening 118 when the internal space R1 is opened.

The first sealing valve 116 which is a part of the movable portion may have a tolerance absorbing portion on a surface in contact with the operation shaft or the first shaft 113. Due to this tolerance absorbing portion, for example, even if there is a difference between the length of the operation shaft or the first shaft 113 in the extending direction and the length of the internal space R1 in the width direction, these errors can be absorbed and the first opening 117 can be sealed, so that the perfume cartridge 101 can prevent the perfume leakage from the first opening 117.

As described above, the tolerance absorbing portion has a structure having a role of absorbing the tolerance of the portion configuring the sealing. Here, the tolerance refers to manufacturing errors and variations of dimensions, such as a distance between the first open/close position of the first opening 117 and the second open/close position of the second opening 118, a width of the opening, and parallelism and a length of a component, related to the sealing. For example, even if the parallelism of the sealing surface is not obtained, the tolerance absorbing portion can maintain a sealed state by absorbing the degree of collapse of the operation shaft or the first shaft 113 by the first spring 114.

Note that although not illustrated, the housing 111 may be provided with a reading unit capable of reading the contents of the perfume cartridge 101. For example, a label, a barcode, or the like may be provided on the surface of the housing 111.

Furthermore, the perfume cartridge 101 can be manufactured by using, for example, a 3D printer. In this case, a material suitable for the 3D printer may be selected as a constituent material of the perfume cartridge 101.

(1-3) Drive Mechanism Portion

Next, a configuration example of the drive mechanism portion applied to the scent providing device 100 according to the present embodiment will be described.

The drive mechanism portion includes a drive mechanism accommodation portion. The drive mechanism portion is connected to the operation shaft that is a movable portion and the first shaft 113 in the perfume cartridge 101, and has a role of a drive mechanism that drives these shafts. Note that the drive mechanism accommodation portion has a cylindrical shape as an example, but the outer shape of the drive mechanism portion according to the present technology is not limited to a cylindrical shape, and can be adapted to the perfume retaining member to have, for example, a column, a rectangular parallelepiped, a cube, or any other appropriate shape.

The drive mechanism portion can include, inside the drive mechanism accommodation portion, a pusher connected to the operation shaft and a shape memory alloy SMA of a thin wire which is a drive source for driving the pusher. A rear end of the pusher is fixed to a drive mechanism fixing portion provided at the inner rear end of the drive mechanism accommodation portion. An SMA sliding portion for folding back and sliding the shape memory alloy SMA is provided near the distal end of the pusher.

The pusher is movable inside the drive mechanism accommodation portion in the extending direction by expansion and contraction of the shape memory alloy SMA. The shape of the pusher may be any shape as long as the pusher pushes the operation shaft, and may be a columnar shape, a conical shape, a cylindrical shape, a prismatic shape, or the like.

For example, a magnet (not illustrated) is attached to the front of the drive mechanism accommodation portion on the perfume cartridge 101 side, and the drive mechanism accommodation portion can be detachably connected to the rear of the connection unit 110 of the perfume cartridge 101 by the magnet. As described above, the perfume cartridge 101 can be easily attached to and detached from the drive mechanism portion by magnet-chucking an attachment and detachment portion to and from the drive mechanism portion. Note that the attachment and detachment portion is detachable by a drive source and/or a magnetic means, and may be a valve connection. Moreover, the power of the linear motion from the drive mechanism portion can be transmitted to the perfume cartridge 101. Therefore, it becomes unnecessary that the perfume cartridge 101 includes a drive source.

The shape memory alloy SMA is folded back in a U-shape at the SMA sliding portion provided near the distal end of the pusher and passes through the inside of the pusher, and both ends thereof are fixed to the drive mechanism fixing portion located at the rear end of the pusher. In the drive mechanism portion, the shape memory alloy SMA as a drive source is energized from a wiring 145, so that the shape memory alloy SMA is contracted while sliding via the SMA sliding portion. When the shape memory alloy SMA is contracted, the drive mechanism fixing portion connected to the end portion of the shape memory alloy SMA moves the pusher toward the front perfume cartridge 101. When the pusher moves forward, the operation shaft connected to the distal end of the pusher pushes out the first sealing valve 116 forward. Moreover, when the first sealing valve 116 is pushed forward, the first shaft 113 connected to the first sealing valve 116 pushes the second sealing valve forward. Note that the drive mechanism portion is a mechanism that does not apply a load to the shape memory alloy SMA in a non-energized state. Furthermore, although the shape memory alloy SMA is used as an example, the present invention is not limited thereto, and an elastic body or the like capable of moving the pusher in a front-rear direction may be used.

Moreover, an actuator as a drive source is not limited to the shape memory alloy SMA, and is only required to be, for example, a linear motion mechanism, such as a motor, a solenoid, a linear slide type, a pneumatic (air pump type), or a small electromagnet, which linearly moves the pusher. Here, the linear motion mechanism includes not only a case where one member moves in the linear direction but also a case where a part of a plurality of members connected to each other moves in the linear direction.

(2) Operation Example of Scent Providing Device

Figure 3:
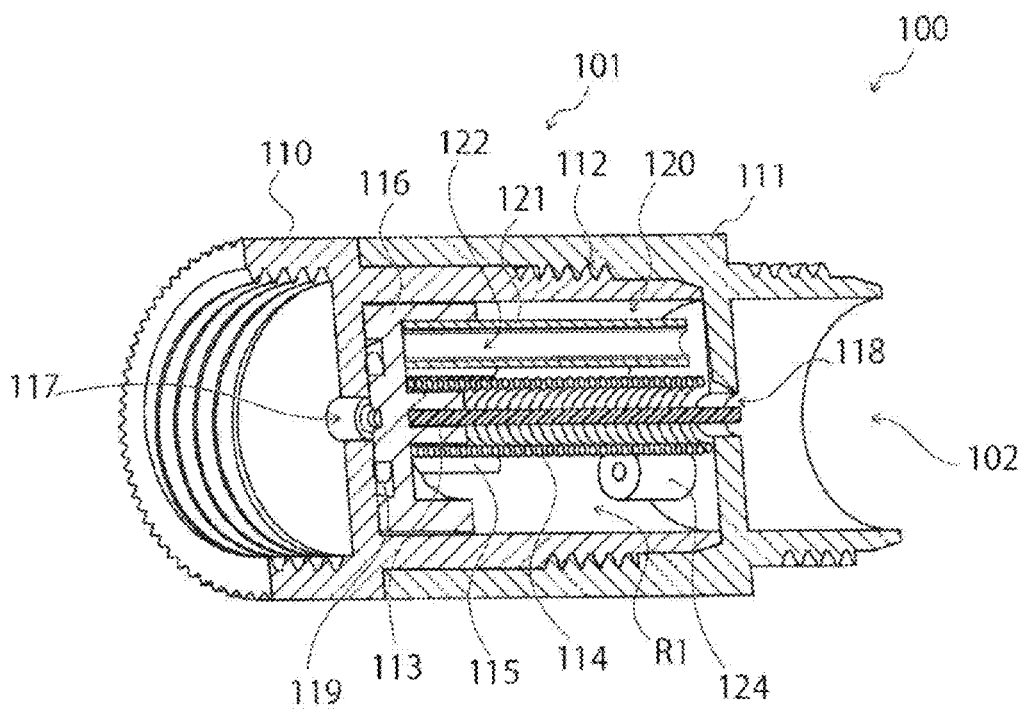
FIG. 3 is a cross-sectional perspective view illustrating an operation example of the scent providing device according to the first embodiment of the present technology.

Next, an example of an operation of releasing the flavored air from the scent providing device 100 will be described with reference to FIGS. 2 and 3. FIG. 3 is a cross-sectional perspective view illustrating an operation example of the scent providing device 100.

First, the perfume stored in the perfume storage unit 120 is released to the outside to permeate the perfume retainer 115. For example, the housing 111 is rotated and screwed into the connection unit 110 to tighten the threaded portion 112.

As the housing 111 rotates, the perfume releasing mechanism 124 inside the housing 111 also rotates, and the perfume releasing mechanism 124 pushes down the perfume storage unit 120. Then, the glass pipe 122 breaks at a portion where the stress concentrates in the perfume storage unit 120, and the stored perfume is released to the outside.

The released perfume permeates and is retained in the perfume retainer 115. At this time, when a perfume absorber that absorbs the perfume released into the perfume storage unit 120 is provided, the perfume can be filled in the perfume retainer 115 by using a capillary phenomenon from the perfume absorber. After the perfume is filled in the perfume retainer 115, the process proceeds to an operation of providing scent.

In the operation of providing scent, first, an air pump (not illustrated) that supplies air connected to an air intake port of the drive mechanism accommodation portion is turned on, and air introduced from the air pump is sent into the drive mechanism accommodation portion. This air pump is an aspect of the blowing source, and is driven by electric power supplied from a battery of a primary battery or a secondary battery to introduce air into a ventilation flow path. The air pump may be, for example, a diaphragm type pump that deforms a diaphragm by supplying an alternating current to a piezoelectric element to suck and pump air.

Next, when the shape memory alloy SMA passing through the inside of the pusher is energized, the shape memory alloy SMA contracts rearward from the pusher. Therefore, the drive mechanism fixing portion connected to the end portion of the pusher linearly moves the pusher toward the front side of the scent providing device 100.

Then, the operation shaft attached to the front of the pusher also moves forward, the operation shaft pushes the first sealing valve 116 forward, and the first sealing valve 116 moves forward. At this time, the first spring 114 is compressed by being pressed forward from the operation shaft.

When the first sealing valve 116 moves forward, the first opening 117 sealed by the first sealing valve 116 is opened to open the internal space R1 to the outside. When the first opening 117 is opened, the air flow sent to the drive mechanism accommodation portion flows into the internal space R1 from the first opening 117 through the connection unit 110.

The air flow having flowed into the internal space R1 mixes with the perfume contained in the perfume retainer 115 provided in the internal space R1, so as to create a mixed flavored air flow. At this time, since the perfume retainer 115 is arranged outside the first spring 114, the wind passing through the internal space R1 easily hits the perfume retainer 115, so that the amount of perfume discharged can be increased.

Moreover, when the first sealing valve 116 moves, the first shaft 113 attached to the front of the first sealing valve 116 also moves forward, and the first shaft 113 pushes the sealing valve, which seals the second opening 118, forward to open the second opening 118.

When the second opening 118 is opened, the internal space R1 is opened to the outside, and the flavored air flow mixed with the perfume in the internal space R1 passes through the second opening 118 and is released from the discharge hole 102 to the outside user.

When the power of the actuator is stopped after the flavored air flow is released to the outside, the contracted state of the shape memory alloy SMA in the non-energized state is released. Then, the operation shaft and the first sealing valve 116 are pushed to the original positions by the restoring force of the compressed first spring 114, so that the pusher returns to the original position in the fixed time. Furthermore, the first sealing valve 116 slides rearward by the restoring force of the first spring 114 until the first sealing valve 116 comes into contact with the first opening 117 and is sealed. With such a sliding capping mechanism by the first sealing valve 116, the first opening 117 can be sealed in the fixed time. At this time, by providing the tolerance absorbing portion, the first opening 117 can be sealed even in a case where a tolerance occurs.

Note that the scent providing device 100 can adjust the amount of tolerance absorption by the tolerance absorbing portion by adjusting the amount of force and displacement of the first spring 114, the shape memory alloy SMA, and the actuator to adjust the elastic force of the first spring 114 sufficient for sealing and the amount of movement of the pusher sufficient for opening.

Furthermore, the scent providing device 100 may be a mechanism that opens and closes with a time difference, for example, from opening the first opening 117 to opening the second opening 118 in order to increase the discharge force from the discharge hole 102, or may be a mechanism that simultaneously opens and closes the first opening 117 and the second opening 118 in order to increase the responsiveness.

Here, when a long period of time has elapsed before use of the conventional perfume cartridge, deterioration of the perfume cannot be avoided. Furthermore, the conventional perfume cartridge has problems such as inconvenience in handling and occurrence of odor transfer during assembly.

On the other hand, according to the scent providing device 100 including the perfume cartridge 101 according to the present embodiment, the perfume storage unit 120 that stores perfume is provided inside the housing 111, and thus the perfume can be confined in the perfume storage unit 120 in a period until the perfume cartridge 101 is used. During use, by breaking the perfume storage unit 120, the perfume is filled in the perfume retainer 115 by using the capillary phenomenon from the perfume absorber provided in the perfume storage unit 120. Therefore, the perfume cartridge 101 is easy to handle and can store the perfume for a long period of time without leaking the perfume.

By the first spring 114, the perfume cartridge 101 can attached in a state where the first sealing valve 116 is sealed. In the first sealing valve 116 which is the movable portion of the perfume cartridge 101, a load direction by the spring force of the first spring 114 is one direction, so that no action and reaction occurs, and the spring force directly becomes the sealing force of the first opening 117. Therefore, the sealing force of the first opening 117 can be increased, so that the first opening 117 can be opened and closed with a small force. Furthermore, since the perfume cartridge 101 can open and close the first opening 117 with a small force, the perfume cartridge can be opened and closed only by air pressure.

In the perfume cartridge 101, since the first opening 117, the second opening 118, the operation shaft, the first shaft 113, the first sealing valve 116, the first spring 114, and the perfume retainer 115 are arranged in the same cylindrical space substantially parallel to the extending direction of the housing 11, the space of the internal space R1 can be saved. Therefore, the perfume cartridge 101 can be downsized.

Furthermore, since the internal space R1 of the perfume cartridge 101 can be closed to a certain pressure, the valve of the air supply path portion can be opened after the pump or the like for ventilation is turned on. Therefore, the scent providing device 100 can maintain intake and exhaust of air in one direction, prevent backflow, protect devices, and prevent contamination (mixing of perfume).

Moreover, in a case where the tolerance absorbing portion is provided, it is possible to structurally control which of the first opening 117 which is the air supply path or the second opening 118 which is the release path of the flavored air is opened first by the tolerance absorbing structure. Therefore, the scent providing device 100 can prevent backflow, protect devices, and prevent contamination by first opening the second opening 118 and then opening the first opening 117 or first closing the second opening 118 and then closing the first opening 117.

Note that in the perfume cartridge 101, in order to prevent permeation of gas, an oil seal material or an elastic material such as silicone rubber or fluorine rubber can be applied to the fitting portion of the connection unit 110 and the housing 111, and a material obtained by combining the oil seal material and the elastic material can also be used. For a similar purpose, the perfume cartridge 101 may have a surface including a material selected from any one of a fluororesin having low gas permeability, a polymer film or a SAM film, an assembly, such as an LB film, of organic polymers or organic low molecules, an organic metal, a metal, a metal film, or a combination of a plurality of these. The metal or the metal film can be used for metal vapor deposition. Moreover, the perfume cartridge 101 may have an inner wall surface including metal.

(3) Modification of Perfume Storage Unit

Figure 4:
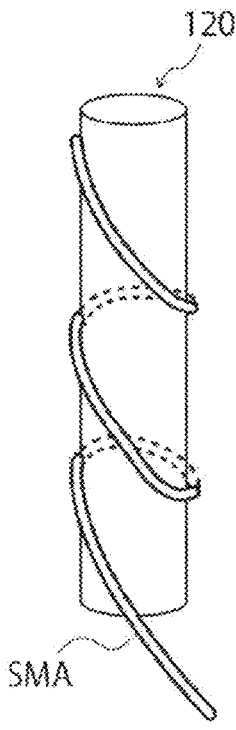
FIG. 4 is a perspective view illustrating a modification of a perfume storage unit according to the first embodiment of the present technology.
Figure 5:
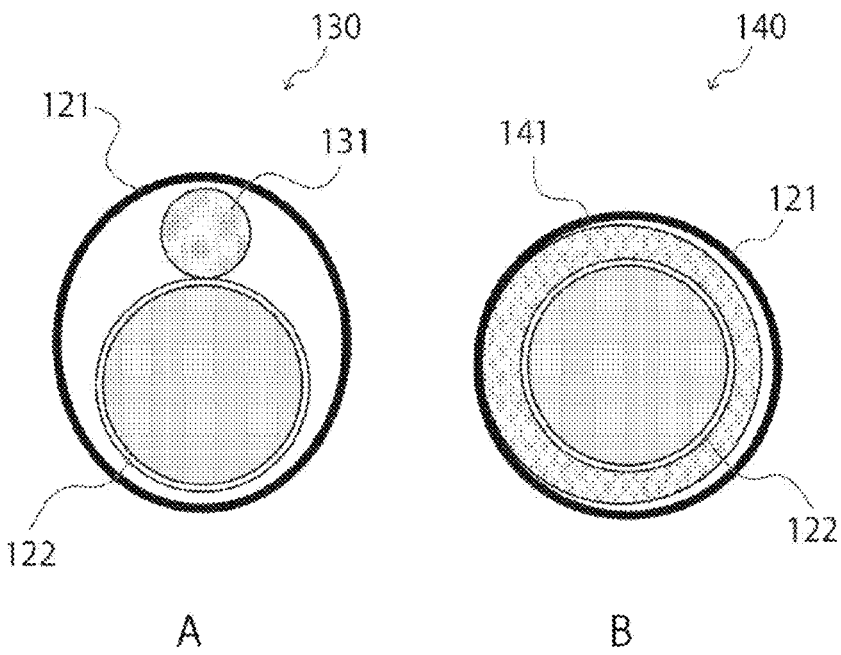
FIG. 5 is a cross-sectional view in a direction perpendicular to an extending direction, illustrating the modification of the perfume storage unit according to the first embodiment of the present technology.

Next, a modification of the perfume storage unit included in the perfume cartridge 101 will be described with reference to FIGS. 4 and 5. FIG. 4 is a perspective view illustrating a first modification of the perfume storage unit 120 according to the present embodiment. FIGS. 5A and 5B are cross-sectional views in a direction perpendicular to the extending direction of the perfume retainer, illustrating a second modification and a third modification of the perfume storage unit 120, respectively.

As illustrated in FIG. 4, the perfume storage unit 120 according to the first modification has a side surface around which a string-shaped shape memory alloy SMA is wound. When the perfume is released from the perfume storage unit 120 according to the first modification, the perfume is released by tightening and breaking the perfume storage unit 120 with the shape memory alloy SMA.

Furthermore, as illustrated in FIG. 5A, the perfume storage unit 130 according to the second modification has the glass pipe 122 that stores perfume in the heat-shrinkable tube 121, and has, between the heat-shrinkable tube 121 and the glass pipe 122, a perfume absorption unit 131 that absorbs the perfume released from the glass pipe 122 to promote the transition to the perfume retainer 115. The perfume absorption unit 131 is arranged at a position adjacent to the glass pipe 122.

Furthermore, as illustrated in FIG. 5B, the perfume storage unit 140 according to the third modification has, between the heat-shrinkable tube 121 and the glass pipe 122, a perfume absorption unit 141 that absorbs the perfume released from the glass pipe 122 to promote the transition to the perfume retainer 115. The perfume absorption unit 141 is arranged to cover the periphery of the glass pipe 122.

According to the scent providing device including the perfume cartridge according to the first to third modifications, similarly to the scent providing device 100 including the perfume cartridge 101 according to the present embodiment, handling is simple and the perfume can be stored for a long period of time without leakage. In particular, in a case where the perfume storage units 130 and 140 of the second and third modifications are used, the perfume is filled in the perfume retainers 115 by using the capillary phenomenon from the perfume storage units 130 and 140, so that the transition of the perfume to the perfume retainers 115 can be further promoted.

2. Second Embodiment (1) Configuration Example of Scent Providing Device

Figure 6:
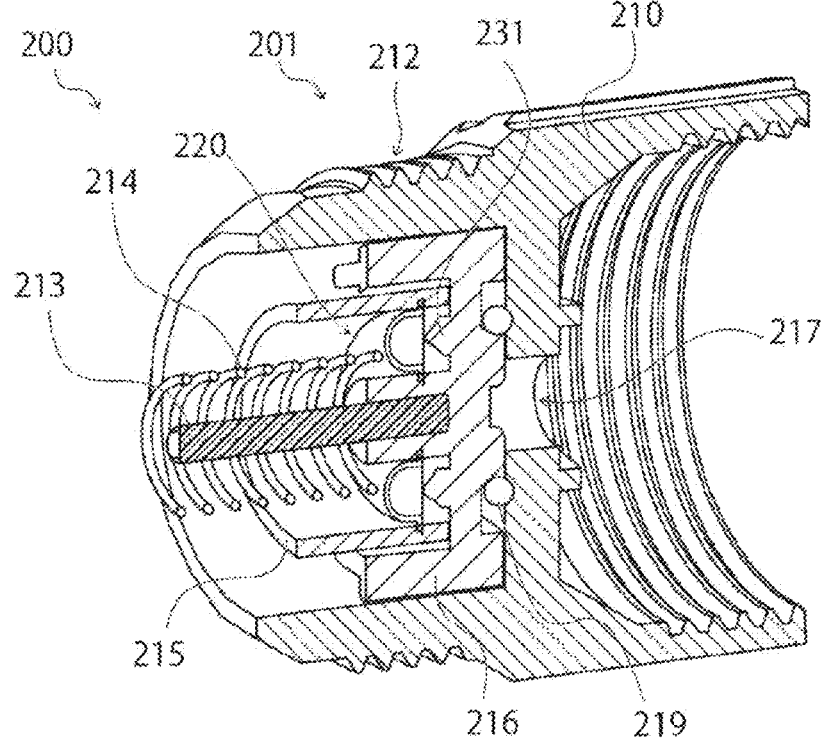
FIG. 6 is a perspective view illustrating a configuration example of a scent providing device according to a second embodiment of the present technology.
Figure 7:
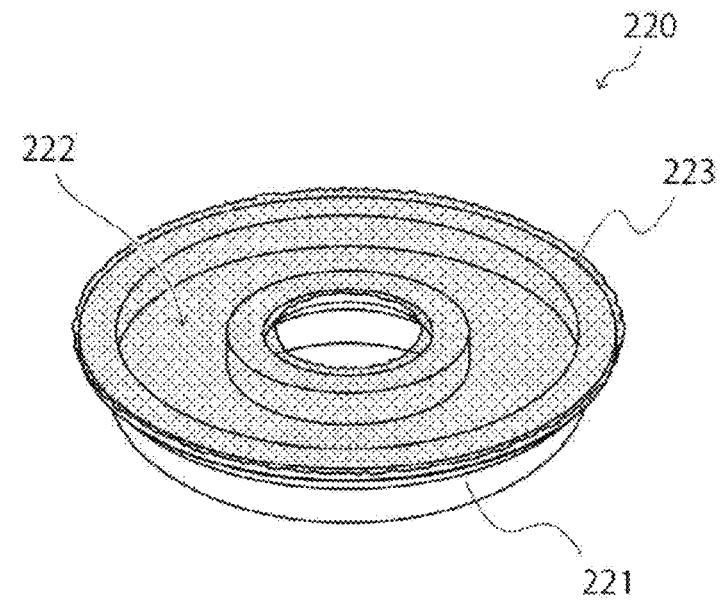
FIG. 7 is a perspective view illustrating a configuration example of a perfume storage unit according to the second embodiment of the present technology.

Next, a configuration example of a scent providing device 200 according to a second embodiment of the present technology will be described with reference to FIGS. 6 and 7. FIG. 6 is a perspective view illustrating the configuration example of the scent providing device 200 according to the present embodiment. FIG. 7 is a perspective view illustrating a configuration example of a perfume storage unit 220 according to the present embodiment as viewed from a bottom surface side.

The scent providing device 200 differs from the scent providing device 100 according to the first embodiment in the structure of the perfume storage unit and the perfume releasing mechanism. Other configurations of the scent providing device 200 are similar to those of the scent providing device 100.

The scent providing device 200 according to the present embodiment includes a perfume cartridge 201 that is a cylindrical perfume retaining member, a cylindrical drive mechanism portion, and the discharge hole 102 that is formed at the distal end of the perfume cartridge 201 and releases flavored air containing perfume to the outside.

As illustrated in FIG. 6, the perfume cartridge 201 includes a connection unit 210 which is detachably connected to a drive mechanism portion which is connected to a movable portion which is movable to open and close the opening and drives the movable portion, and a housing 211 which is connected to the connection unit 210. The drive mechanism portion includes a drive mechanism accommodation portion that accommodates the drive mechanism.

The connection unit 210 is connected in a sealed manner by being screwed with the housing 211 by a threaded portion 212. The connection unit 210 includes an operation shaft therein. In the perfume cartridge 201, the fitting portion with the connection unit 210 can be sealed by the threaded portion 212 to prevent perfume leakage from the fitting portion.

The housing 211 includes the internal space R1, a first opening 217 that opens the internal space R1 to the outside and releases flavored air, in which perfume and air are mixed, toward the discharge hole 102, and a first shaft 213 as an operation shaft and a first spring 214 as an elastic body, the first shaft 213 and the first spring 214 being movable portions which are movable to open and close the first opening 217.

The first shaft 213 is arranged across the central portion of the internal space R1, and the first spring 214 is arranged to surround the periphery of the first shaft 213. A first sealing valve 216 that seals the first opening 217 is connected to the end portion of the first shaft 213 on the first opening 117 side.

The first spring 214 biases the first sealing valve 216 in a direction of sealing the first opening 217. Moreover, in the internal space R1, a perfume retainer 215 such as an impregnating material retaining liquid perfume is arranged to surround the periphery of the first spring 214. As described above, by arranging the perfume retainer 215 outside the first spring 214, the wind passing through the internal space R1 easily hits the perfume retainer 215, and the discharge amount of the perfume can be increased.

In the first sealing valve 216, as an example for enhancing sealing force, an O-ring 219 is attached to a contact surface with a wall surface in which the first opening 217 is formed inside the housing 211. Furthermore, the first shaft 213 or the first spring 214 is provided with the perfume storage unit 220 which is movable together with the first shaft 213 and the first spring 214 and stores perfume in a sealed manner.

As illustrated in FIGS. 6 and 7, as an example, the perfume storage unit 220 includes a main body portion 221 formed in a donut shape with a flat bottom surface and having a groove portion 222 for storing perfume, and a sealing sheet 223 for sealing the bottom surface of the main body portion 221. As the sealing sheet 223, a metal sheet or the like having low gas permeability can be used. The perfume storage unit 220 is fixed to the first shaft 213 or the first spring 214 that is a movable portion.

Furthermore, as illustrated in FIG. 6, a protruding perfume releasing mechanism 231 that breaks through the sealing sheet 223 at the time of release of the perfume is attached to the surface of the first sealing valve 216 facing the bottom surface of the perfume storage unit 220. The perfume releasing mechanism 231 may have any shape and material as long as the perfume releasing mechanism can break through the sealing sheet 223 and release the stored perfume to the outside.

(2) Operation Example of Scent Providing Device

Figure 8:
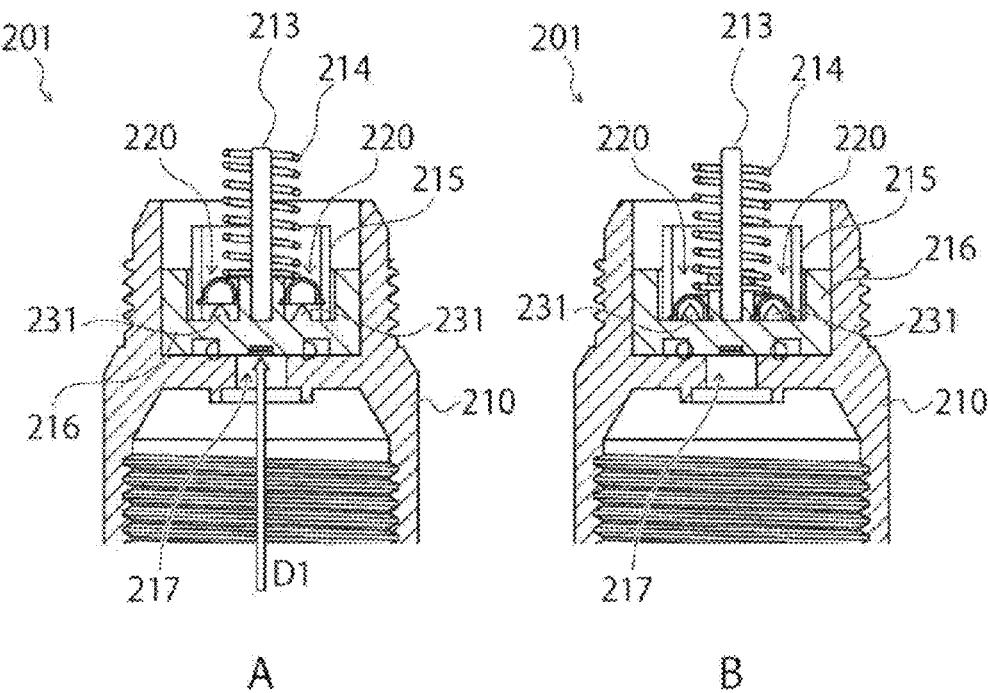
FIG. 8 is a side sectional view illustrating an operation example of the scent providing device according to the second embodiment of the present technology.

Next, an example of an operation of releasing the flavored air from the scent providing device 200 will be described with reference to FIG. 8. FIG. 8A is a side sectional view illustrating a state before the perfume is released from the perfume storage unit 220 of the scent providing device 200. FIG. 8B is a side sectional view illustrating a state where the perfume is released from the perfume storage unit 220 of the scent providing device 200.

Similarly to the scent providing device 100 according to the first embodiment, first, an air pump (not illustrated) which is connected to the air intake port of the drive mechanism accommodation portion and supplies air is turned on, so as to send the air introduced from the air pump into the drive mechanism accommodation portion. This air pump is an aspect of the blowing source, and is driven by electric power supplied from a battery of a primary battery or a secondary battery to introduce air into a ventilation flow path.

Next, when the shape memory alloy SMA connected to the pusher is energized, the shape memory alloy SMA contracts rearward from the pusher. Therefore, the pusher is linearly moved to the front side of the scent providing device 200.

Then, as illustrated in FIG. 8A, the operation shaft attached to the front of the pusher also moves in a movable direction D1 on the front side, the operation shaft pushes the first sealing valve 216 in the movable direction D1, and the first sealing valve 216 moves to the front side. At this time, the first spring 214 is compressed by being pressed forward from the operation shaft.

When the first sealing valve 216 moves forward, the first opening 217 sealed by the first sealing valve 216 is opened to open the internal space R1 to the outside. When the first opening 217 is opened, the air flow sent to the drive mechanism accommodation portion flows into the internal space R1 from the first opening 217 through the connection unit 210.

Moreover, when the operation shaft is moved in the movable direction D1 and the first sealing valve 216 is pushed in the movable direction D1, the perfume releasing mechanism 231 attached to the first sealing valve 216 reaches the bottom surface of the perfume storage unit 220 and breaks through the sealing sheet 223 of the perfume storage unit 220 as illustrated in FIG. 8B. When the sealing sheet 223 is broken, the perfume stored in the perfume storage unit 220 is released to the outside. The released perfume permeates the perfume retainer 215 to be retained therein.

Thereafter, the air flow having flowed into the internal space R1 mixes with the perfume contained in the perfume retainer 215 provided in the internal space R1, so as to create a mixed flavored air flow.

Moreover, when the first sealing valve 216 moves, the first shaft 213 attached to the front of the first sealing valve 216 also moves forward, and the first shaft 213 pushes the sealing valve, which seals the second opening 118, forward to open the second opening 118.

When the second opening 118 is opened, the internal space R1 is opened to the outside, and the flavored air flow mixed with the perfume in the internal space R1 passes through the second opening 118 and is released from the discharge hole 102 to the outside user.

When the power of the actuator is stopped after the flavored air flow is released to the outside, the contracted state of the shape memory alloy SMA in the non-energized state is released. Then, the operation shaft and the first sealing valve 216 are pushed to the original positions by the restoring force of the contracted first spring 214, so that the pusher returns to the original position in the fixed time. Furthermore, the first sealing valve 216 slides rearward by the restoring force of the first spring 214 until the first sealing valve 216 comes into contact with the first opening 217 and is sealed. With such a sliding capping mechanism by the first sealing valve 216, the first opening 217 can be sealed in the fixed time.

According to the scent providing device 200 including the perfume cartridge 201 according to the present embodiment, similarly to the scent providing device 100 according to the first embodiment, handling is simple and the perfume can be stored for a long period of time without leakage. Moreover, according to the scent providing device 200, the perfume flows to the outside from the main body portion 221 of the perfume storage unit 220 only by breaking through the sealing sheet 223 of the perfume storage unit 220, and thus, it is not necessary to provide a perfume absorber in the perfume storage unit 220, and the perfume can be filled in the perfume retainer 215 with a simple configuration.

3. Third Embodiment

(1) Configuration Example of Scent Providing Device

Figure 9:
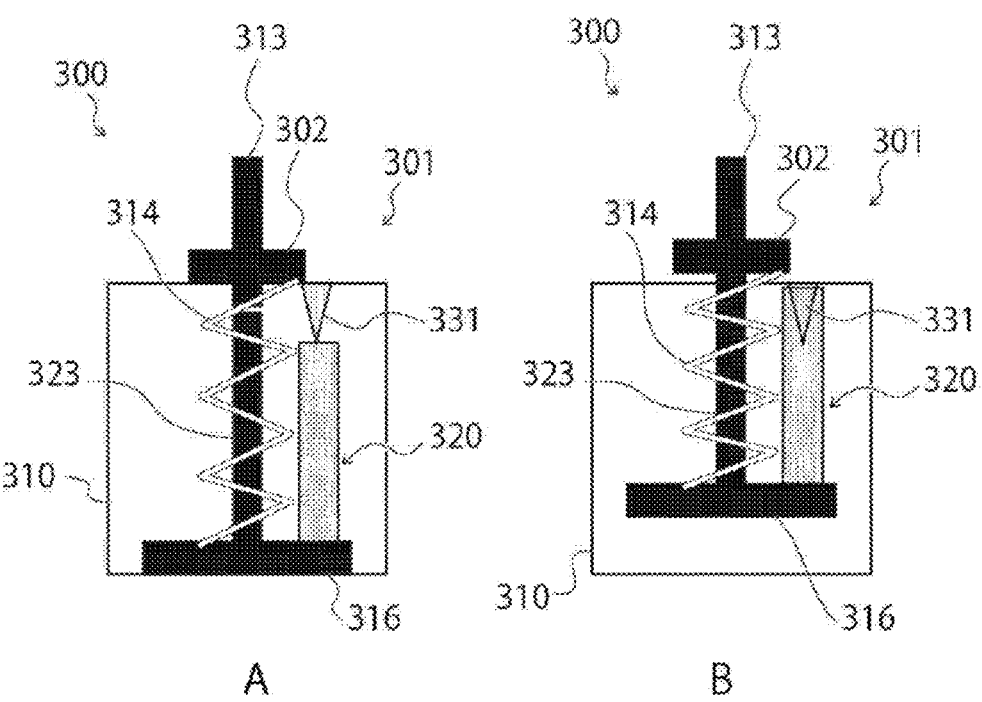
FIG. 9 is a side sectional view illustrating an operation example of a scent providing device according to a third embodiment of the present technology.

Next, a configuration example of a scent providing device 300 according to a third embodiment of the present technology will be described with reference to FIG. 9. FIG. 9A is a side sectional view illustrating a state before the perfume is released from the perfume storage unit 320 of the scent providing device 300. FIG. 9B is a side sectional view illustrating a state where the perfume is released from the perfume storage unit 320 of the scent providing device 300.

The scent providing device 300 differs from the scent providing device 100 according to the first embodiment in that the perfume releasing mechanism has a structure that pierces the end portion of the perfume storage unit. Other configurations of the scent providing device 300 are similar to those of the scent providing device 100.

As illustrated in FIG. 9A, the perfume cartridge 301 included in the scent providing device 300 according to the present embodiment includes a connection unit which is detachably connected to a drive mechanism portion which is connected to a movable portion which is movable to open and close the opening and drives the movable portion, and a housing 310 which is connected to the connection unit.

The housing 310 includes an internal space R1, a first shaft 323 and a first spring 314 as movable portions which are movable to open and close the first opening 117 through which an external air flow flows into the internal space R1, and a second shaft 313 as a movable portion which is movable to open and close the second opening 118 through which the flavored air obtained by mixing perfume and air is released from the internal space R1 toward the discharge hole 102.

The first shaft 323 is arranged across the central portion of the internal space R1, and the first spring 314 is arranged to surround the periphery of the first shaft 323. A first sealing valve 316 that seals the first opening 117 is connected to the end portion of the first shaft 323 on the first opening 117 side.

The second shaft 313 is connected to the first shaft 323, and the end portion on the second opening 118 side is connected with a second sealing valve 302 that seal the second opening 118.

The first spring 314 biases the first sealing valve 316 in a direction of sealing the first opening 117. Moreover, in the internal space R1, a perfume retainer 115 such as an impregnating material retaining liquid perfume is arranged to surround the periphery of the first spring 314.

The perfume storage unit 320 that stores perfume in a sealed manner is provided on the surface side of the first sealing valve 316 facing a contact surface with the housing 310. As an example, the perfume storage unit 320 is formed in a cylindrical shape extending in a direction parallel to the first shaft 323, which is a movable direction of the movable portion, and has one end fixed to the first sealing valve 316.

On the wall surface in which the second opening 118 is formed inside the housing 310, a protruding perfume releasing mechanism 331 is provided at a position where the other end of the perfume storage unit 320 is pierced when the first sealing valve 316 is moved to move the perfume storage unit 320 forward.

The first shaft 323 is a movable portion which is movable to open and close the first opening 117 by the first sealing valve 316, and in the fixed time, the first sealing valve 316 is brought into contact with the first opening 117 by the first spring 314 to be sealed. Therefore, the perfume cartridge 301 can prevent perfume leakage from the first opening 117.

(2) Operation Example of Scent Providing Device

Next, an example of an operation of releasing the perfume from the perfume storage unit 320 of the scent providing device 300 will be described with reference to FIG. 9.

As illustrated in FIG. 9B, when the operation shaft attached to the front of the pusher moves forward, the operation shaft pushes the first sealing valve 316 forward, and the first sealing valve 316 moves forward.

When the first sealing valve 316 moves forward, the first opening 117 sealed by the first sealing valve 316 is opened to open the internal space R1 to the outside. When the first opening 117 is opened, the air flow sent to the drive mechanism accommodation portion flows into the internal space R1 from the first opening 117 through the connection unit.

Moreover, when the operation shaft is moved forward and the first sealing valve 316 is pushed forward, the end portion of the perfume storage unit 320 attached to the first sealing valve 316 pierces the perfume releasing mechanism 331. When the end portion of the perfume storage unit 320 pierces the perfume releasing mechanism 331, the perfume storage unit 320 is broken, and the perfume stored in the perfume storage unit 320 is released to the outside. The released perfume permeates and is retained in the perfume retainer 115.

Thereafter, the air flow that has flowed into the internal space R1 mixes with the perfume contained in the perfume retainer 115 provided in the internal space R1, so as to create a mixed flavored air flow.

According to the scent providing device 300 of the present embodiment, similarly to the scent providing device 100 according to the first embodiment, handling is simple, and the perfume can be stored for a long period of time without leakage.

4. Fourth Embodiment (1) Configuration Example of Scent Providing Device

Figure 10:
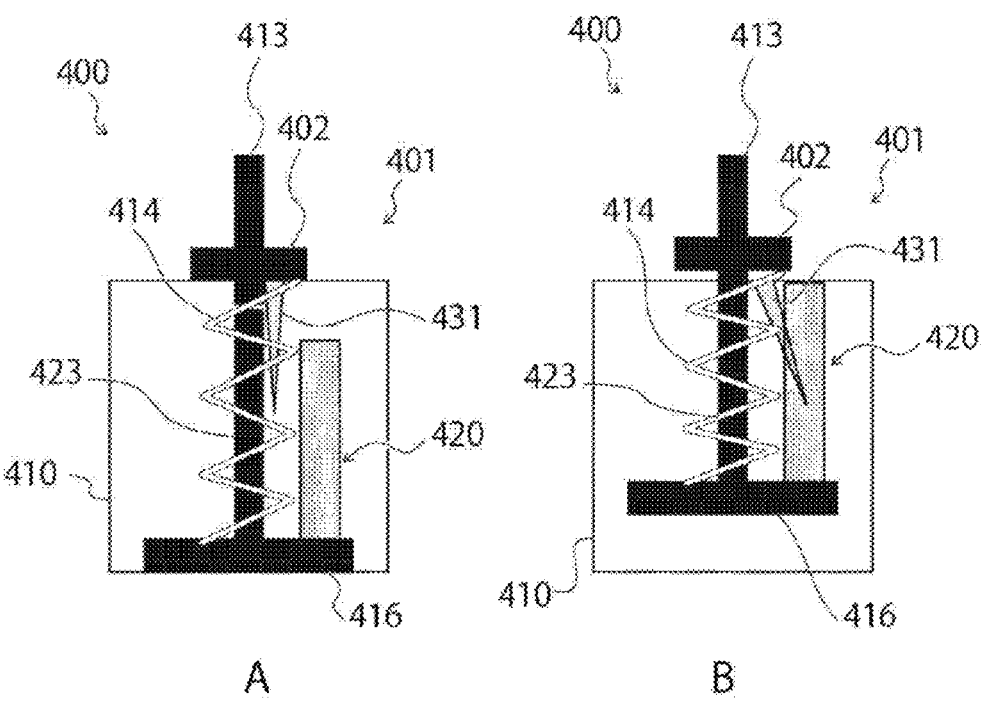
FIG. 10 is a side sectional view illustrating an operation example of a scent providing device according to a fourth embodiment of the present technology.

Next, a configuration example of a scent providing device 400 according to a fourth embodiment of the present technology will be described with reference to FIG. 10. FIG. 10A is a side sectional view illustrating a state before the perfume is released from the perfume storage unit 420 of the scent providing device 400. FIG. 10B is a side sectional view illustrating a state where the perfume is released from the perfume storage unit 420 of the scent providing device 400.

The scent providing device 400 differs from the scent providing device 300 according to the third embodiment in that the perfume releasing mechanism has a structure that pierces the side portion of the perfume storage unit. Other configurations of the scent providing device 400 are similar to those of the scent providing device 300.

As illustrated in FIG. 10A, the perfume cartridge 401 included in the scent providing device 400 according to the present embodiment includes a connection unit which is detachably connected to a drive mechanism portion which is connected to a movable portion which is movable to open and close the opening and drives the movable portion, and a housing 410 which is connected to the connection unit.

The housing 410 includes an internal space R1, a first shaft 423 and a first spring 414 as movable portions which are movable to open and close the first opening 117 through which an external air flow flows into the internal space R1, and a second shaft 413 as a movable portion which is movable to open and close the second opening 118 through which the flavored air obtained by mixing perfume and air is released from the internal space R1 toward the discharge hole 102.

The first shaft 423 is arranged across the central portion of the internal space R1, and the first spring 414 is arranged to surround the periphery of the first shaft 423. A first sealing valve 416 that seals the first opening 117 is connected to the end portion of the first shaft 423 on the first opening 117 side.

The second shaft 413 is connected to the first shaft 423, and the end portion on the second opening 118 side is connected with a second sealing valve 402 that seal the second opening 118.

The first spring 414 biases the first sealing valve 416 in a direction of sealing the first opening 117. Moreover, in the internal space R1, the perfume retainer 115 such as an impregnating material retaining liquid perfume is arranged to surround the periphery of the first spring 414.

The perfume storage unit 420 that stores perfume in a sealed manner is provided on the surface side of the first sealing valve 416 facing a contact surface with the housing 410. As an example, the perfume storage unit 420 is formed in a cylindrical shape extending in a direction parallel to the first shaft 323, which is a movable direction of the movable portion, and has one end fixed to the first sealing valve 416.

On the wall surface in which the second opening 118 is formed inside the housing 410, a protruding perfume releasing mechanism 431 is provided at a position where the side surface portion of the perfume storage unit 420 is pierced when the first sealing valve 416 is moved to move the perfume storage unit 420 forward.

The first shaft 423 is a movable portion which is movable to open and close the first opening 117 by the first sealing valve 416, and in the fixed time, the first sealing valve 416 is brought into contact with the first opening 117 by the first spring 414 to be sealed. Therefore, the perfume cartridge 401 can prevent perfume leakage from the first opening 117.

(2) Operation Example of Scent Providing Device

Next, an example of an operation of releasing the perfume from the perfume storage unit 420 of the scent providing device 400 will be described with reference to FIG. 10.

As illustrated in FIG. 10B, when the operation shaft attached to the front of the pusher moves forward, the operation shaft pushes the first sealing valve 416 forward, and the first sealing valve 416 moves forward.

When the first sealing valve 416 moves forward, the first opening 117 sealed by the first sealing valve 416 is opened to open the internal space R1 to the outside. When the first opening 117 is opened, the air flow sent to the drive mechanism accommodation portion flows into the internal space R1 from the first opening 117 through the connection unit.

Moreover, when the operation shaft is moved forward and the first sealing valve 416 is pushed forward, the perfume storage unit 420 attached to the first sealing valve 416 approaches the perfume releasing mechanism 431. In parallel with this operation, the distal end of the perfume releasing mechanism 431 moves to a position where the distal end pierces the side surface portion of the perfume storage unit 420. Then, the distal end of the perfume releasing mechanism 431 pierces the side surface portion of the perfume storage unit 420.

When the perfume releasing mechanism 431 pierces the side surface portion of the perfume storage unit 420, the perfume storage unit 420 is broken, and the perfume stored in the perfume storage unit 420 is released to the outside. The released perfume permeates and is retained in the perfume retainer 115.

Thereafter, the air flow that has flowed into the internal space R1 mixes with the perfume contained in the perfume retainer 115 provided in the internal space R1, so as to create a mixed flavored air flow.

According to the scent providing device 400 of the present embodiment, similarly to the scent providing device 300 according to the third embodiment, handling is simple and the perfume can be stored for a long period of time without leakage.

5. Fifth Embodiment (1) Configuration Example of Scent Providing Device

Figure 11:
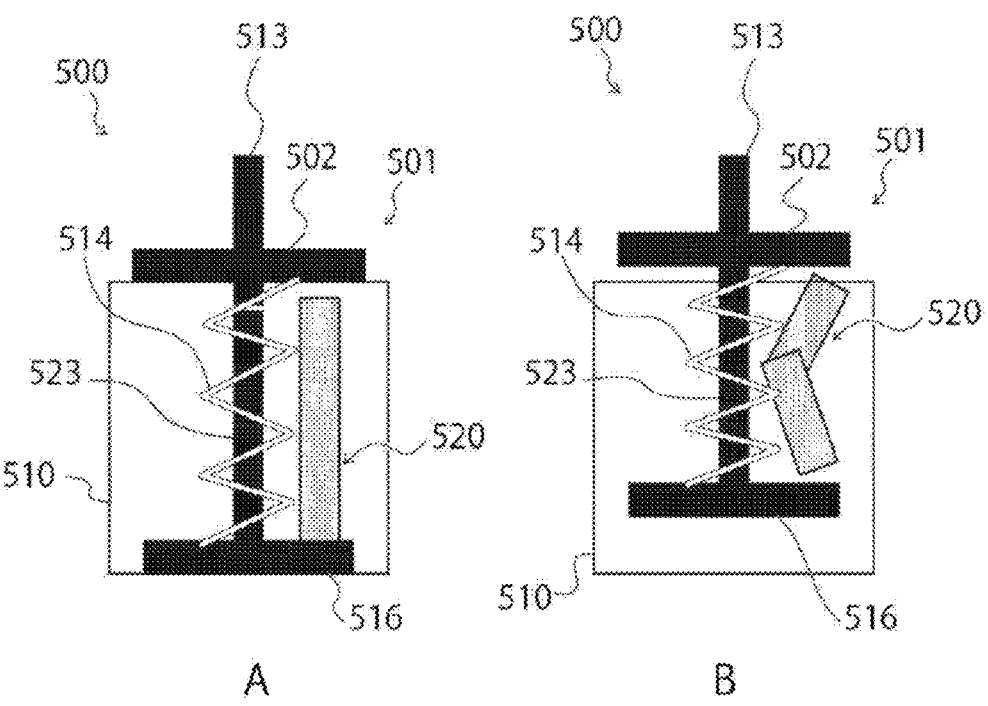
FIG. 11 is a side sectional view illustrating an operation example of a scent providing device according to a fifth embodiment of the present technology.

Next, a configuration example of a scent providing device 500 according to a fifth embodiment of the present technology will be described with reference to FIG. 11. FIG. 11A is a side sectional view illustrating a state before the perfume is released from the perfume storage unit 520 of the scent providing device 500. FIG. 11B is a side sectional view illustrating a state where the perfume is released from the perfume storage unit 520 of the scent providing device 500.

The scent providing device 500 differs from the scent providing device 300 according to the third embodiment in that the perfume releasing mechanism has a structure that folds and breaks the perfume storage unit. Other configurations of the scent providing device 500 are similar to those of the scent providing device 300.

As illustrated in FIG. 11A, the perfume cartridge 501 included in the scent providing device 500 according to the present embodiment includes a connection unit which is detachably connected to a drive mechanism portion which is connected to a movable portion which is movable to open and close the opening and drives the movable portion, and a housing 510 which is connected to the connection unit.

The housing 510 includes an internal space R1, a first shaft 523 and a first spring 514 as movable portions which are movable to open and close the first opening 117 through which an external air flow flows into the internal space R1, and a second shaft 513 as a movable portion which is movable to open and close the second opening 118 through which the flavored air obtained by mixing perfume and air is released from the internal space R1 toward the discharge hole 102.

The first shaft 523 is arranged across the central portion of the internal space R1, and the first spring 514 is arranged to surround the periphery of the first shaft 523. A first sealing valve 516 that seals the first opening 117 is connected to the end portion of the first shaft 523 on the first opening 117 side.

The second shaft 513 is connected to the first shaft 523, and the end portion on the second opening 118 side is connected with a second sealing valve 502 that seals the second opening 118.

The second sealing valve 502 extends in a direction intersecting a direction in which the first sealing valve 516 moves, and comes into contact with the end portion of the perfume storage unit 520 when the first sealing valve 516 moves to move the perfume storage unit 520 forward. Therefore, the perfume storage unit 520 can be sandwiched between the first sealing valve 516 and the second sealing valve 502 to be folded and broken. Therefore, in the present embodiment, the first sealing valve 516 and the second sealing valve 502 have a role of the perfume releasing mechanism.

The first spring 514 biases the first sealing valve 516 in a direction of sealing the first opening 117. Moreover, in the internal space R1, the perfume retainer 115 such as an impregnating material retaining liquid perfume is arranged to surround the periphery of the first spring 514.

The perfume storage unit 520 that stores perfume in a sealed manner is provided on the surface side of the first sealing valve 516 facing a contact surface with the housing 510. As an example, the perfume storage unit 520 is formed in a cylindrical shape extending in a direction parallel to the first shaft 523, which is a movable direction of the movable portion, and has one end fixed to the first sealing valve 516.

The first shaft 523 is a movable portion which is movable to open and close the first opening 117 by the first sealing valve 516, and in the fixed time, the first sealing valve 516 is brought into contact with the first opening 117 by the first spring 514 to be sealed. Therefore, the perfume cartridge 501 can prevent perfume leakage from the first opening 117.

(2) Operation Example of Scent Providing Device

Next, an example of an operation of releasing the perfume from the perfume storage unit 520 of the scent providing device 500 will be described with reference to FIG. 11.

As illustrated in FIG. 11B, when the operation shaft attached to the front of the pusher moves forward, the operation shaft pushes the first sealing valve 516 forward, and the first sealing valve 516 moves forward.

When the first sealing valve 516 moves forward, the first opening 117 sealed by the first sealing valve 516 is opened to open the internal space R1 to the outside. When the first opening 117 is opened, the air flow sent to the drive mechanism accommodation portion flows into the internal space R1 from the first opening 117 through the connection unit.

Moreover, when the operation shaft is moved forward and the first sealing valve 516 is pushed forward, the perfume storage unit 520 attached to the first sealing valve 516 approaches the second sealing valve 502 serving as the perfume releasing mechanism. Then, the end portion of the perfume storage unit 520 comes into contact with the second sealing valve 502, and the perfume storage unit 520 is sandwiched between the first sealing valve 516 and the second sealing valve 502 to be folded and broken.

When the perfume storage unit 520 is broken, the perfume stored in the perfume storage unit 520 is released to the outside. The released perfume permeates and is retained in the perfume retainer 115.

Thereafter, the air flow that has flowed into the internal space R1 mixes with the perfume contained in the perfume retainer 115 provided in the internal space R1, so as to create a mixed flavored air flow.

According to the scent providing device 500 of the present embodiment, similarly to the scent providing device 300 according to the third embodiment, handling is simple and the perfume can be stored for a long period of time without leakage.

6. Sixth Embodiment (1) Configuration Example of Perfume Cartridge

Figure 12:
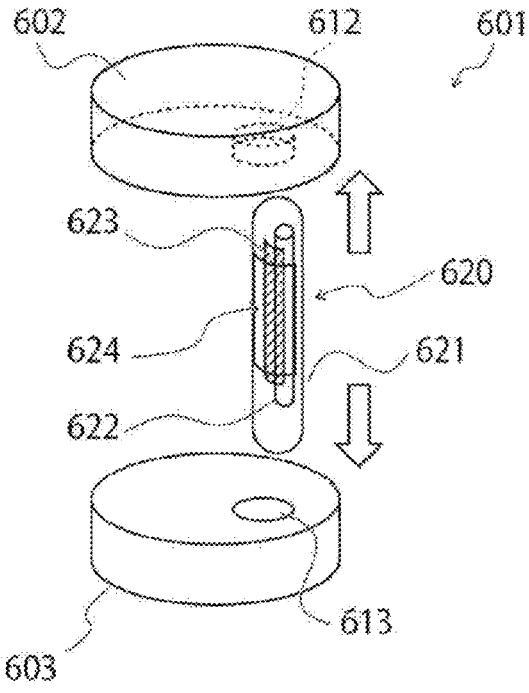
FIG. 12 is an exploded perspective view illustrating a configuration example of a perfume retaining member according to a sixth embodiment of the present technology.

Next, a configuration example of a perfume cartridge 601 according to a sixth embodiment of the present technology will be described with reference to FIG. 12. FIG. 12 is an exploded perspective view illustrating an aspect state where a perfume storage unit 620 is incorporated in the perfume cartridge 601. The perfume cartridge 601 is broken by twisting the perfume storage unit 620 by the perfume releasing mechanism.

As illustrated in FIG. 12, the perfume cartridge 601 according to the present embodiment includes, inside the housing, the perfume storage unit 620 that stores perfume in a sealed manner. Moreover, the perfume cartridge 601 includes, inside the housing, a first rotating body 602 and a second rotating body 603 which have disk shapes and are connected to one end and the other end of the perfume storage unit 620, respectively. The first rotating body 602 and the second rotating body 603 are formed with a fixing groove 612 and a fixing groove 613 for fixing one end and the other end of the perfume storage unit 620, respectively.

The perfume storage unit 620 includes a plastic case 621 having a hollow inside, a glass pipe 622 stored in the plastic case 621, and a perfume absorption unit 623 arranged adjacent to the glass pipe 622. The plastic case 621 is formed with an opening 624 for releasing stored perfume to the outside.

(2) Operation Example of Perfume Cartridge

Figure 13:
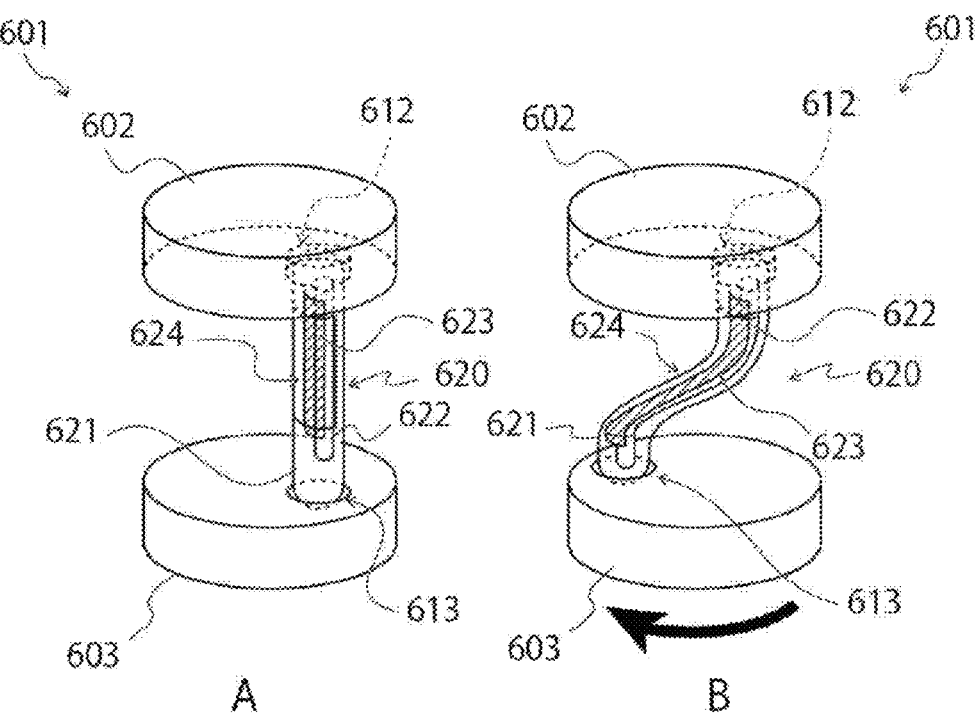
FIG. 13 is a perspective view illustrating an operation example of the perfume retaining member according to the sixth embodiment of the present technology.

Next, an example of an operation of releasing the perfume from the perfume storage unit 620 of the perfume cartridge 601 will be described with reference to FIG. 13. FIG. 13A is a perspective view illustrating a state before the perfume is released from the perfume storage unit 620 of the perfume cartridge 601. FIG. 13B is a perspective view illustrating a state where the perfume is released from the perfume storage unit 620.

As illustrated in FIG. 13A, in a state where the perfume is stored in the perfume storage unit 620 and the perfume is not released, the perfume storage unit 620 is fixed in a direction substantially perpendicular to the opposing surfaces of the first rotating body 602 and the second rotating body 603.

When the perfume is released from the perfume storage unit 620, as illustrated in FIG. 13B, one of the first rotating body 602 and the second rotating body 603 is fixed, and the other is rotated in a direction perpendicular to the extending direction of the perfume storage unit 620. Alternatively, both the first rotating body 602 and the second rotating body 603 are reversely rotated in the direction perpendicular to the extending direction of the perfume storage unit 620.

When the first rotating body 602 and/or the second rotating body 603 are rotated, the perfume storage unit 620 fixed to the first rotating body 602 and the second rotating body 603 is twisted, and the glass pipe 622 in the plastic case 621 is broken.

When the glass pipe 622 is broken, the perfume stored in the glass pipe 622 is released to the outside and absorbed by the adjacent perfume absorption units 623. When the perfume absorption unit 623 absorbs the perfume, the perfume can be caused to permeate into the perfume retainer 115 from the opening 624 of the plastic case 621 by using the capillary phenomenon from the perfume absorption unit 623.

According to the scent providing device including the perfume cartridge 601 according to the present embodiment, similarly to the scent providing device 100 according to the first embodiment, handling is simple and the perfume can be stored for a long period of time without leakage.

7. Seventh Embodiment

Figure 14:
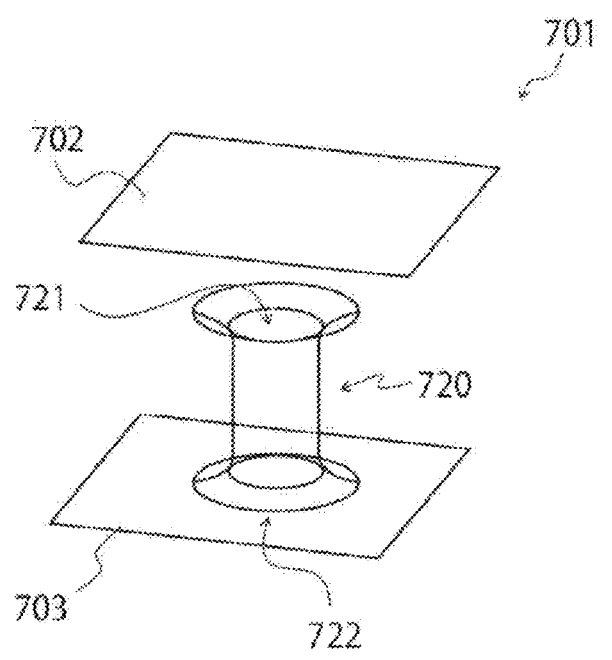
FIG. 14 is a perspective view illustrating a configuration example of a perfume retaining member according to a seventh embodiment of the present technology.

Next, a configuration example of a perfume cartridge 701 according to a seventh embodiment of the present technology will be described with reference to FIG. 14. FIG. 14 is a perspective view illustrating a perfume storage unit 720 included in the perfume cartridge 701. The perfume cartridge 701 is broken by breaking through the perfume storage unit 720 by the perfume releasing mechanism.

As illustrated in FIG. 14, the perfume cartridge 701 according to the present embodiment includes, inside the housing, the perfume storage unit 720 that stores perfume in a sealed manner. Moreover, the perfume cartridge 701 includes a protruding perfume releasing mechanism (not illustrated) inside the housing.

The perfume storage unit 720 is formed in a cylindrical shape, and both ends thereof are formed with an opening 721 and an opening 722. The opening 721 and the opening 722 are attached with a sealing sheet 702 and a sealing sheet 703 that seal and close respective openings.

When the perfume is released from the perfume storage unit 720, a protruding perfume releasing mechanism provided inside the housing of the perfume cartridge 701 breaks through the sealing sheet 702 and the sealing sheet 703 attached to the opening 721 and the opening 722, and the stored perfume is released to the outside.

According to the scent providing device including the perfume cartridge 701 according to the present embodiment, similarly to the scent providing device 100 according to the first embodiment, handling is simple and the perfume can be stored for a long period of time without leakage.

8. Eighth Embodiment (1) Configuration Example of Perfume Cartridge

Figure 15:
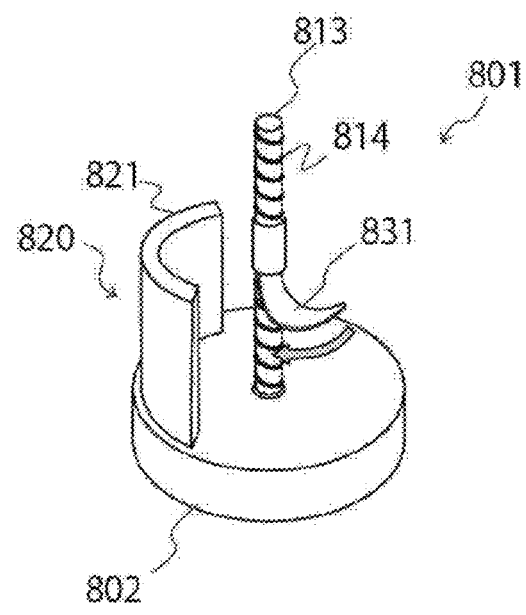
FIG. 15 is a perspective view illustrating a configuration example of a perfume retaining member according to an eighth embodiment of the present technology.

Next, a configuration example of a perfume cartridge 801 according to an eighth embodiment of the present technology will be described with reference to FIG. 15. FIG. 15 is a partial perspective view illustrating a perfume storage unit 820 included in the perfume cartridge 801. The perfume cartridge 801 is broken by cutting a part of the perfume storage unit 820 by the perfume releasing mechanism.

As illustrated in FIG. 15, the perfume cartridge 801 according to the present embodiment includes, inside the housing, a disk-shaped fixing base 802, a first shaft 813 vertically attached to the central portion of the fixing base 802, and a first spring 814 arranged around the first shaft 813. The first shaft 813 can be movable in an extending direction perpendicular to the surface of the fixing base 802, and can also be rotated in an axial direction.

Furthermore, on the surface of the fixing base 802, the perfume storage unit 820 having a curved surface along the circumference is arranged in the vicinity of the circumference, as an example. The perfume storage unit 820 has, for example, a glass pipe of which the surface is covered with the plastic case 821, and one end thereof is fixed to the surface of the fixing base 802. Moreover, a perfume releasing mechanism 831 having a blade that rotates in accordance with the rotation of the first shaft 813 and cuts the side surface of the perfume storage unit 820 is attached to the side surface of the first shaft 813.

(2) Operation Example of Perfume Cartridge

Next, an example of an operation of releasing the perfume from the perfume storage unit 820 of the perfume cartridge 801 will be described with reference to FIG. 15.

When the perfume is released from the perfume storage unit 820 of the perfume cartridge 801, as illustrated in FIG. 15, the perfume releasing mechanism 831 is rotated by rotating the first shaft 813 with respect to the fixing base 802.

When the perfume releasing mechanism 831 is rotated, the blade of the perfume releasing mechanism 831 comes into contact with the side surface of the plastic case 821 and the glass pipe, the side surface of the plastic case 821 and the glass pipe is cut, and the perfume storage unit 820 is broken.

When the perfume storage unit 820 is broken, the perfume stored in the perfume storage unit 820 is released to the outside. The released perfume permeates and is retained in the perfume retainer 115.

According to the scent providing device including the perfume cartridge 801 according to the present embodiment, similarly to the scent providing device 100 according to the first embodiment, handling is simple and the perfume can be stored for a long period of time without leakage.

9. Ninth Embodiment (1) Configuration Example of Scent Providing Device

Figure 16:
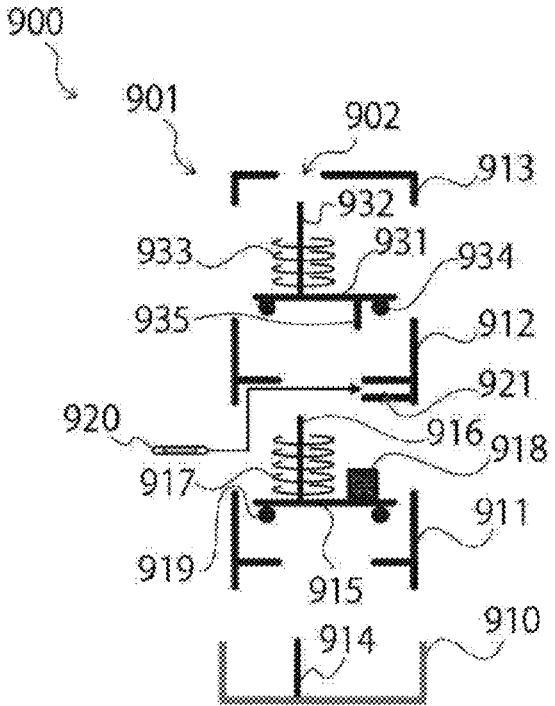
FIG. 16 is a schematic diagram illustrating a configuration example of a scent providing device according to a ninth embodiment of the present technology.
Figure 17:
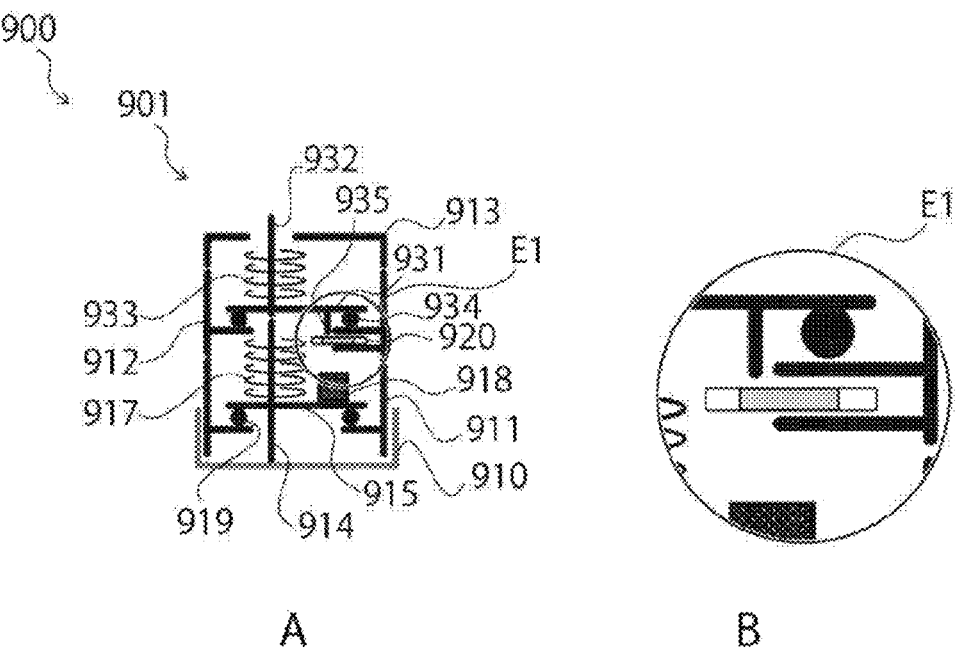
FIG. 17 is a schematic diagram illustrating a configuration example of a perfume retaining member according to the ninth embodiment of the present technology.

Next, a configuration example of a scent providing device 900 according to a ninth embodiment of the present technology will be described with reference to FIGS. 16 and 17. FIG. 16 is a schematic diagram illustrating the configuration example of the scent providing device 900 according to the present embodiment. FIG. 17A is a schematic diagram illustrating the configuration example of a perfume cartridge

901 according to the present embodiment. FIG. 17B is a partially enlarged view of the inside of the perfume cartridge 901.

The scent providing device 900 differs from the scent providing device 100 according to the first embodiment in that a lid to be used for opening the perfume storage unit is included.

The scent providing device 900 according to the present embodiment includes a perfume cartridge 901 that is a cylindrical perfume retaining member, a cylindrical drive mechanism portion, and a discharge hole 902 that is formed at the distal end of the perfume cartridge 901 and releases flavored air containing perfume to the outside. Moreover, the scent providing device 900 includes a lid 910 serving as a tool that stably fixes the inside during standby or transportation and opens the perfume storage unit during use.

As illustrated in FIG. 16, the perfume cartridge 901 includes a connection unit 911 which is detachably connected to a drive mechanism portion which is connected to a movable portion which is movable to open and close the opening and drives the movable portion, a housing 912 which is connected to the connection unit 911, and a housing distal end portion 913 which is attached to the distal end portion of the housing 912. The drive mechanism portion includes a drive mechanism accommodation portion that accommodates the drive mechanism.

A pin 914 is formed inside the lid 910. The connection unit 911 includes a sealing valve 915, a shaft 916 which is an operation shaft, and a spring 917. The connection unit 911 includes an impregnating material 918 on the upper surface of the sealing valve 915, and includes an O-ring 919 on the lower surface of the sealing valve 915.

The housing 912 includes, at the bottom, a perfume storage unit 920 and a perfume storage unit fixing portion 921 that fixes the perfume storage unit 920. Furthermore, the housing 912 includes a sealing valve 931, a shaft 932 as an operation shaft, and a spring 933. Moreover, the housing 912 further includes, on the lower surface of the sealing valve 931, an O-ring 934 and an opening pin 935 for opening the perfume storage unit 920.

(2) Operation Example of Scent Providing Device

Figure 18:
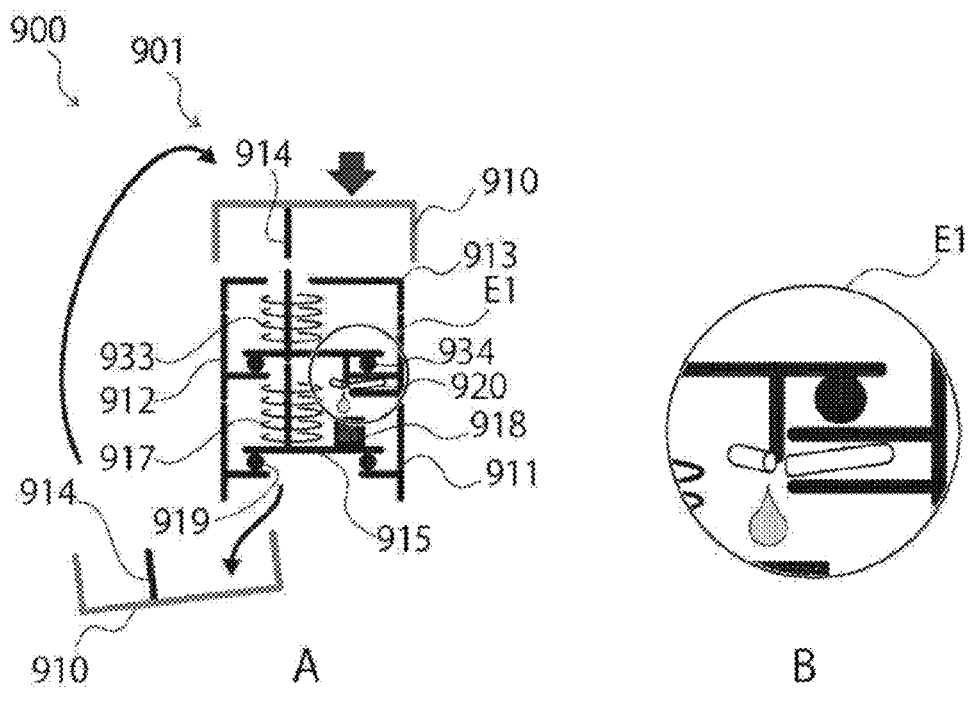
FIG. 18 is a schematic diagram illustrating an operation example of the scent providing device according to the ninth embodiment of the present technology.
Figure 19:
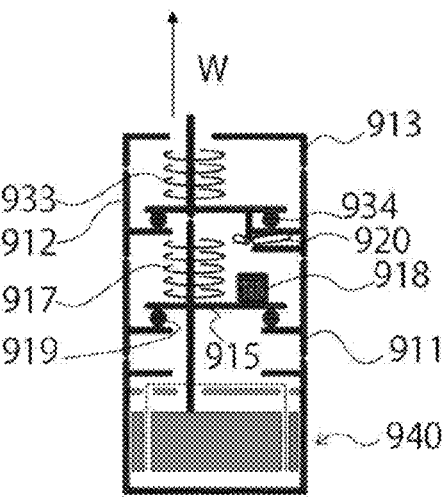
FIG. 19 is a schematic diagram illustrating the operation example of the scent providing device according to the ninth embodiment of the present technology.

Next, an example of an operation of releasing the flavored air from the scent providing device 900 will be described with reference to FIGS. 17 to 19. FIG. 18A is a schematic diagram illustrating an operation example of the scent providing device 900. FIG. 18B is a partially enlarged view of the inside of the perfume cartridge 901 when the perfume storage unit 920 is opened. FIG. 19 is a schematic diagram illustrating the operation example of the scent providing device 900.

As illustrated in FIG. 17, in the scent providing device 900, during standby or transportation, the pin 914 of the lid 910 pushes up the sealing valve 915 and the sealing valve 931, preventing the opening pin 935 from moving downward to press and open the perfume storage unit 920.

As illustrated in FIG. 18A, during use, the lid 910 attached below is removed, the lid 910 is covered from the discharge hole 902 side, and the pin 914 is inserted into the inside from the discharge hole 902. Then, the lid 910 is pushed into the perfume cartridge 901.

Then, the sealing valve 931 is pushed down by the pin 914 via the shaft 932, and as illustrated in FIG. 18B, the opening pin 935 attached to the lower surface of the sealing valve 931 pierces the perfume storage unit 920 to open the perfume storage unit 920.

As illustrated in FIG. 19, after the perfume released from the perfume storage unit 920 is impregnated into the impregnating material 918, the drive mechanism portion 940 is connected to the rear of the connection unit 911. Then, the perfume is sprayed from the discharge hole 902 to the outside together with the air sent into the scent providing device 900 by the drive mechanism portion 940.

According to the scent providing device 900 including the perfume cartridge 901 according to the present embodiment, similarly to the scent providing device 100 according to the first embodiment, handling is simple and the perfume can be stored for a long period of time without leakage. Furthermore, according to the scent providing device 900, it is possible to enhance storage stability and prevent erroneous opening while preventing odor transfer due to internal perfume at the time of assembly. Moreover, according to the scent providing device 900, it is possible to determine whether or not the perfume cartridge 901 has been used by checking whether or not the lid 910 is attached to the lower portion.

10. Tenth Embodiment (1) Configuration Example of Scent Providing Unit

Figure 20:
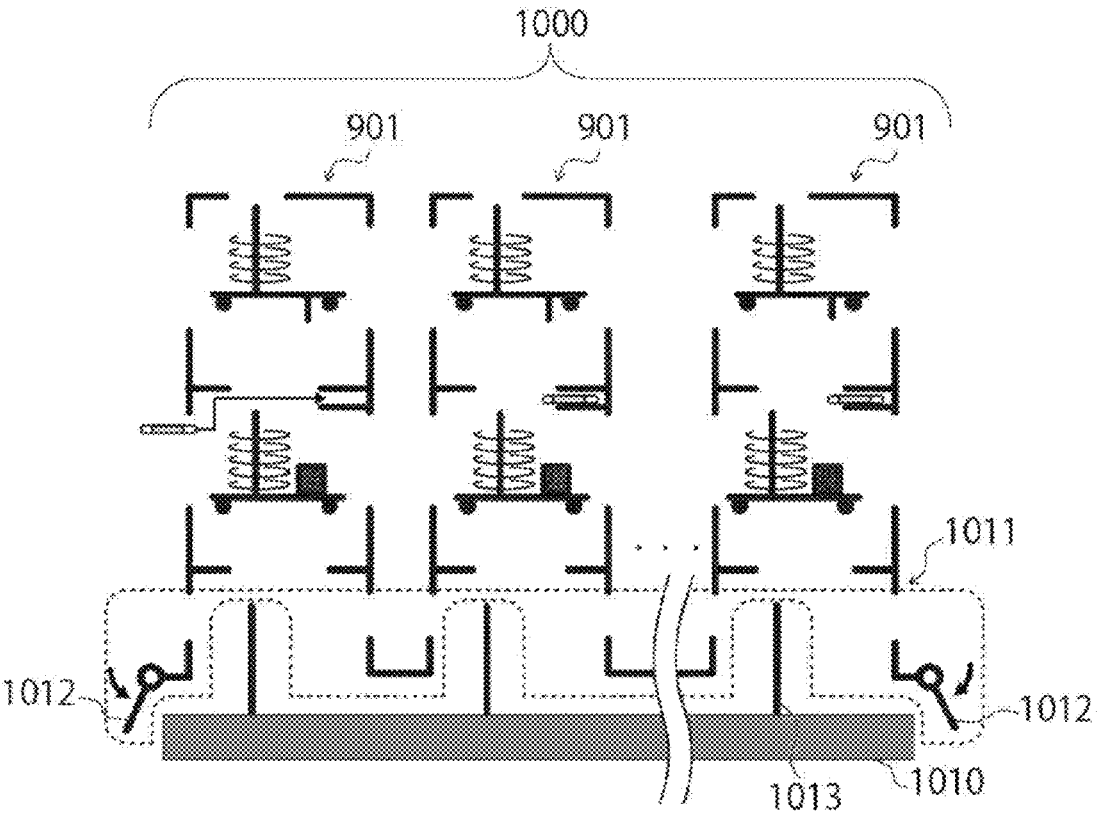
FIG. 20 is a schematic diagram illustrating a configuration example of a scent providing device according to a tenth embodiment of the present technology.

Next, a configuration example of a scent providing unit 1000 according to a tenth embodiment of the present technology will be described with reference to FIG. 20. FIG. 20 is a schematic diagram illustrating the configuration example of the scent providing unit 1000 according to the present embodiment.

The scent providing unit 1000 includes a plurality of perfume cartridges 901, and opens the perfume storage units 920 included therein at once.

The scent providing unit 1000 according to the present embodiment includes the plurality of perfume cartridges 901, a lid 1010 attached below, and a fixing unit 1011 that fixes the plurality of perfume cartridges 901 to the lid 1010.

The lid 1010 has a plurality of pins 1013. The fixing unit 1011 includes a connection unit 1012 connected to the lid 1010.

(2) Operation example of Scent Providing Unit

Next, an example of an operation of releasing the flavored air from the scent providing unit 1000 will be described with reference to FIGS. 21 to 25. FIGS. 21 to 25 are schematic diagrams illustrating the operation example of the scent providing unit 1000.

Figure 21:
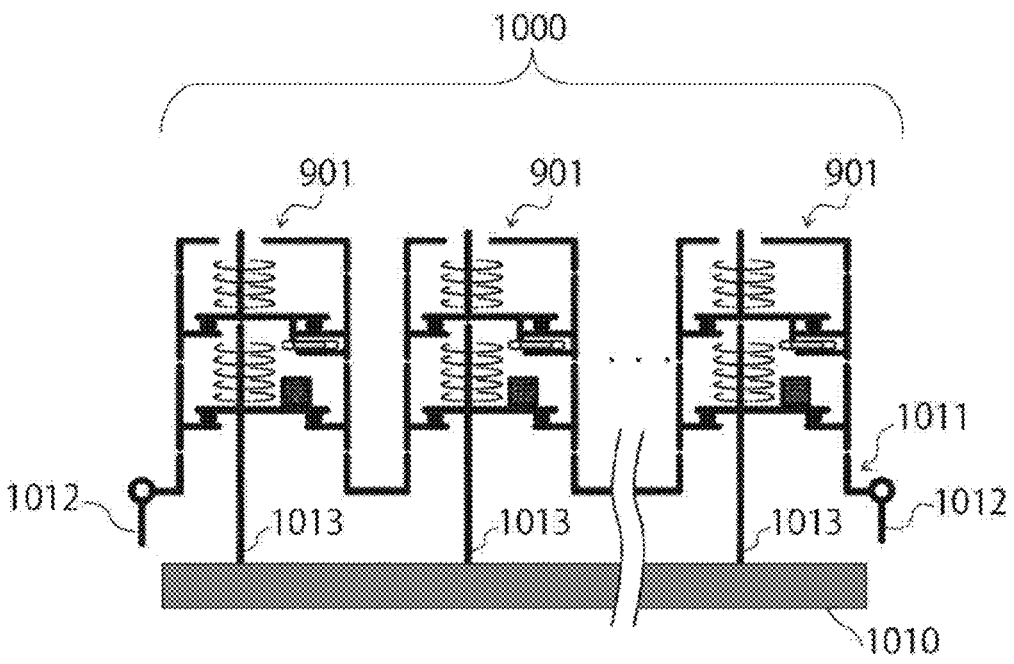
FIG. 21 is a schematic diagram illustrating an operation example of the scent providing device according to the tenth embodiment of the present technology.

As illustrated in FIG. 21, in the scent providing unit 1000, the lid 1010 is fixed to the lower portion with the fixing unit 1011 during standby or transportation. Then, the plurality of pins 1013 of the lid 1010 pushes up the sealing valve 915 and the sealing valve 931 of each perfume cartridge 901, preventing the opening pin 935 from moving downward to press and open the perfume storage unit 920.

Figure 22:
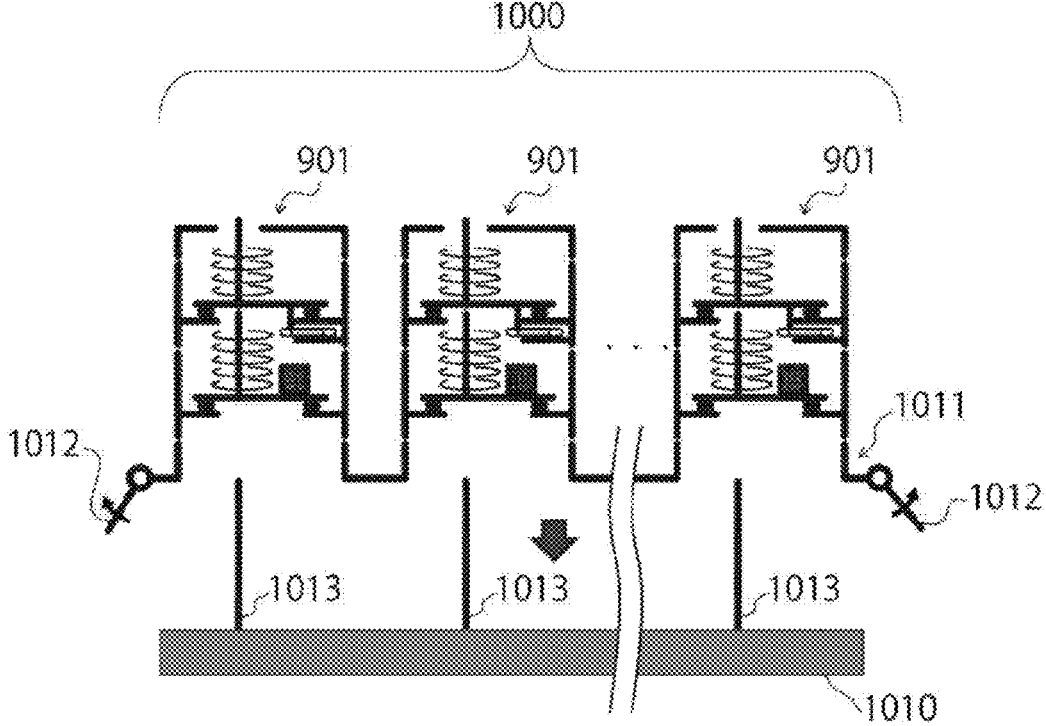
FIG. 22 is a schematic diagram illustrating the operation example of the scent providing device according to the tenth embodiment of the present technology.

As illustrated in FIG. 22, during use, the lid 1010 attached below is removed, the lid 1010 is covered from the discharge hole 902 side, and the plurality of pins 1013 is inserted into the inside from the discharge hole 902 of each perfume cartridge 901. Then, the lid 1010 is pushed into each perfume cartridge 901.

Figure 23:
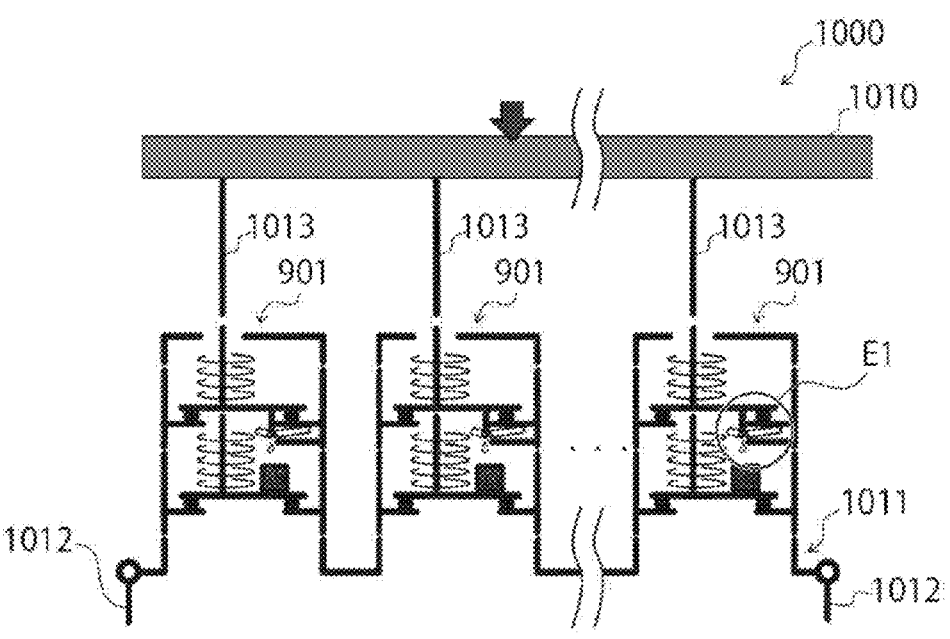
FIG. 23 is a schematic diagram illustrating the operation example of the scent providing device according to the tenth embodiment of the present technology.

Then, as illustrated in FIG. 23, the sealing valve 931 is pushed down by the plurality of pins 1013 via the shafts 932, and the opening pin 935 attached to the lower surface of the sealing valve 931 pierces the perfume storage unit 920 to open each perfume storage unit 920.

Figure 24:
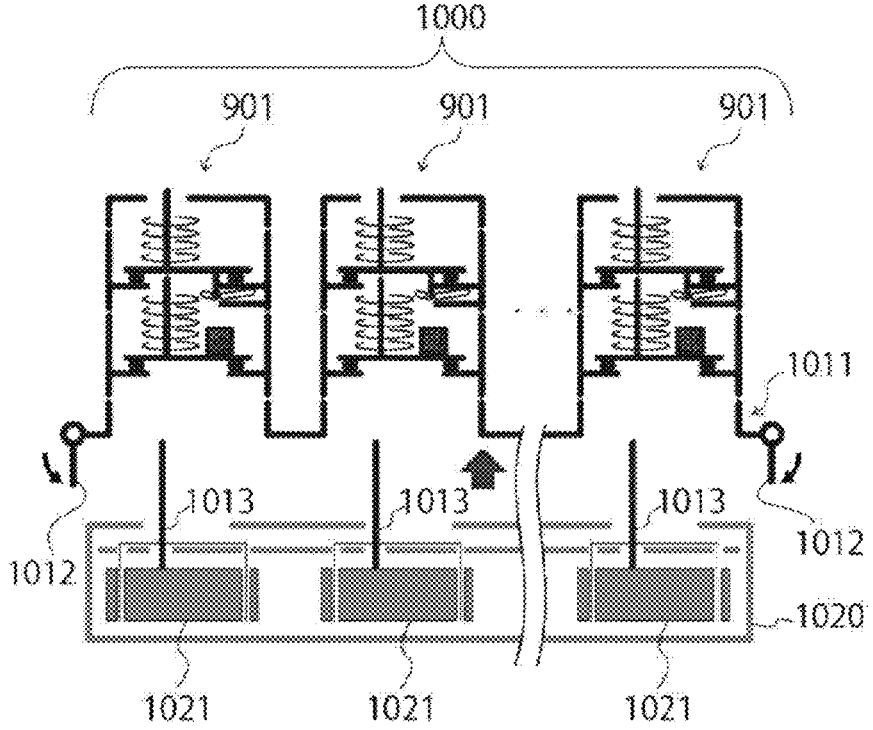
FIG. 24 is a schematic diagram illustrating the operation example of the scent providing device according to the tenth embodiment of the present technology.
Figure 25:
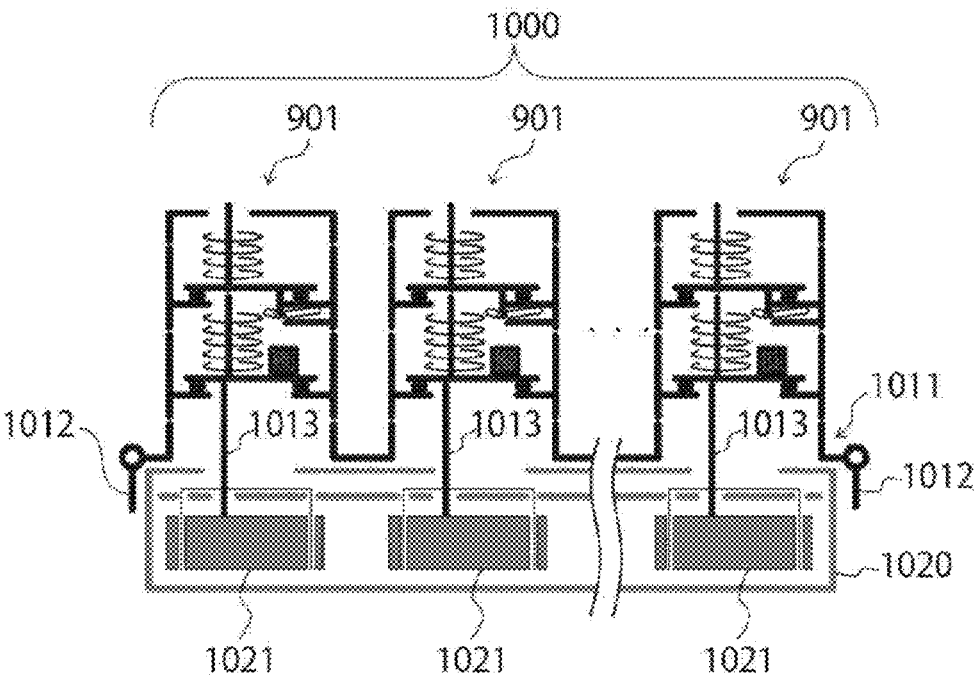
FIG. 25 is a schematic diagram illustrating the operation example of the scent providing device according to the tenth embodiment of the present technology.

As illustrated in FIGS. 24 and 25, after the perfume released from the perfume storage unit 920 is impregnated into the impregnating material 918, a drive mechanism unit 1020 having a plurality of drive mechanism portions 1021 is connected to the lower portion of the fixing unit 1011. Then, the perfume is sprayed from each of the discharge holes 902 to the outside together with the air sent into the scent providing unit 1000 by each of the drive mechanism portions 1021.

The scent providing unit 1000 according to the present embodiment can achieve effects similar to those of the scent providing device 900 according to the ninth embodiment.

11. Eleventh Embodiment

Figure 26:
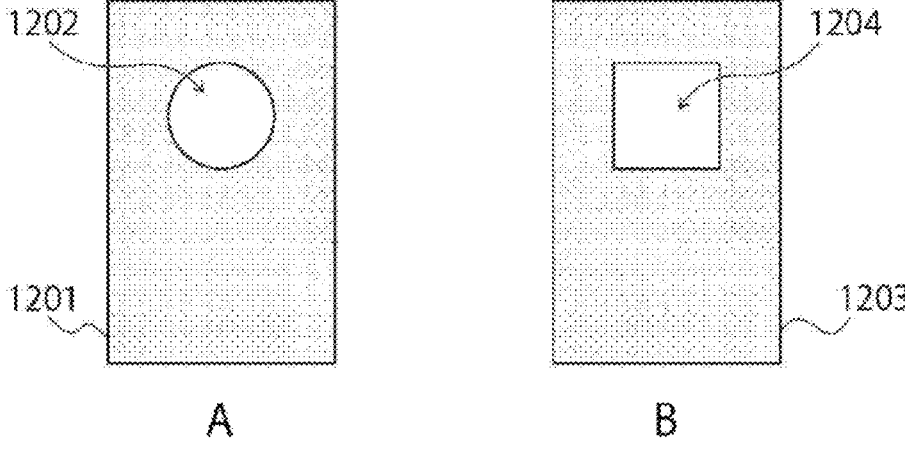
FIG. 26 is a schematic diagram illustrating a configuration example of a perfume retaining member according to an eleventh embodiment of the present technology.

Next, a configuration example of a perfume cartridge according to an eleventh embodiment of the present technology will be described with reference to FIG. 26. FIGS. 26A and 26B are schematic diagrams illustrating the configuration example of an impregnating material in the perfume cartridge according to the present embodiment.

As illustrated in FIGS. 26A and 26B, the perfume cartridge according to the present embodiment can be used by the perfume storage unit passing through the hole of the impregnating material 1201 or 1203 in which a circular hole 1202 or a rectangular hole 1204 is formed. Note that the hole formed in the impregnating material is not limited to these shapes, and may have any shape as long as the perfume storage unit passes through the hole to be retained.

12. Twelfth Embodiment

Figure 27:
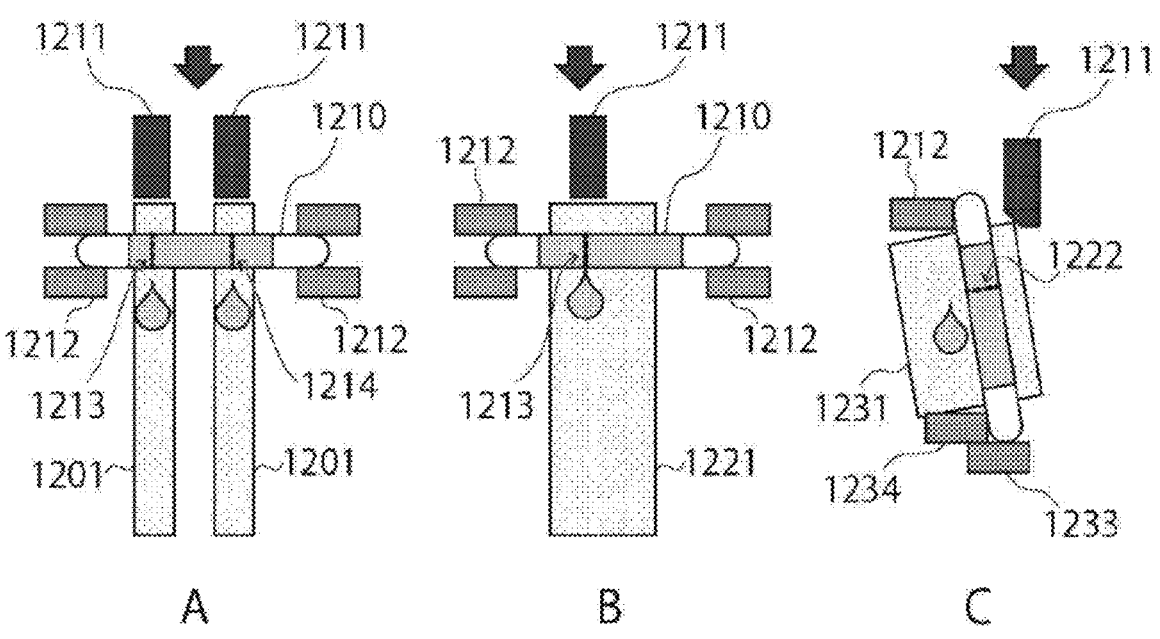
FIG. 27 is a schematic diagram illustrating a configuration example of a perfume retaining member according to a twelfth embodiment of the present technology.

Next, a configuration example of a perfume cartridge according to a twelfth embodiment of the present technology will be described with reference to FIG. 27. FIGS. 27A to 27C are schematic diagrams illustrating a method of opening the perfume cartridge according to the present embodiment.

As illustrated in FIG. 27A, in the perfume cartridge according to the present embodiment, a perfume storage unit 1210 laterally passes through the respective holes formed in two impregnating materials 1201, and both ends of the perfume storage units 1210 are fixed by perfume storage unit fixing portions 1212. Furthermore, the perfume storage unit 1210 has a damaged portion 1213 and a damaged portion 1214 formed with a cutter or the like in portions which correspond to the positions of the respective holes formed in the two impregnating materials 1201 when passing through the holes. A force is applied to the two impregnating materials 1201 with an opening pin 1211 or the like to open the perfume storage unit 1210, and the stored perfume can be impregnated into each of the impregnating materials 1201 from the damaged portion 1213 and the damaged portion 1214.

Furthermore, as illustrated in FIG. 27B, in the perfume cartridge according to the present embodiment, the perfume storage unit 1220 laterally passes through a hole formed in a thick impregnating material 1221, and both ends of the perfume storage unit 1220 are fixed by the perfume storage unit fixing portions 1212. Furthermore, the perfume storage unit 1220 has a damaged portion 1222 formed with a cutter or the like in a portion which corresponds to the position of the hole formed in the impregnating material 1221 when passing through the hole. A force is applied to the impregnating material 1221 with the opening pin 1211 or the like to open the perfume storage unit 1210, and the stored perfume can be impregnated into the impregnating material 1221 from the damaged portion 1222.

Furthermore, as illustrated in FIG. 27C, in the perfume cartridge according to the present embodiment, the perfume storage unit 1220 vertically passes through a hole formed in a thick impregnating material 1231, the upper end side surface of the perfume storage unit 1220 is fixed by the perfume storage unit fixing portion 1212, and the lower end and the lower end side surface of the perfume storage unit 1220 are fixed by a perfume storage unit fixing portion 1233 and a perfume storage unit fixing portion 1234. Furthermore, the perfume storage unit 1220 has the damaged portion 1222 formed with a cutter or the like in a portion which corresponding to the position of the hole formed in the impregnating material 1231 when passing through the hole. A force is applied to the impregnating material 1231 with an opening pin 1232 or the like to open the perfume storage unit 1220, and the stored perfume can be impregnated into the impregnating material 1231 from the damaged portion 1222.

13. Thirteenth Embodiment

Figure 28:
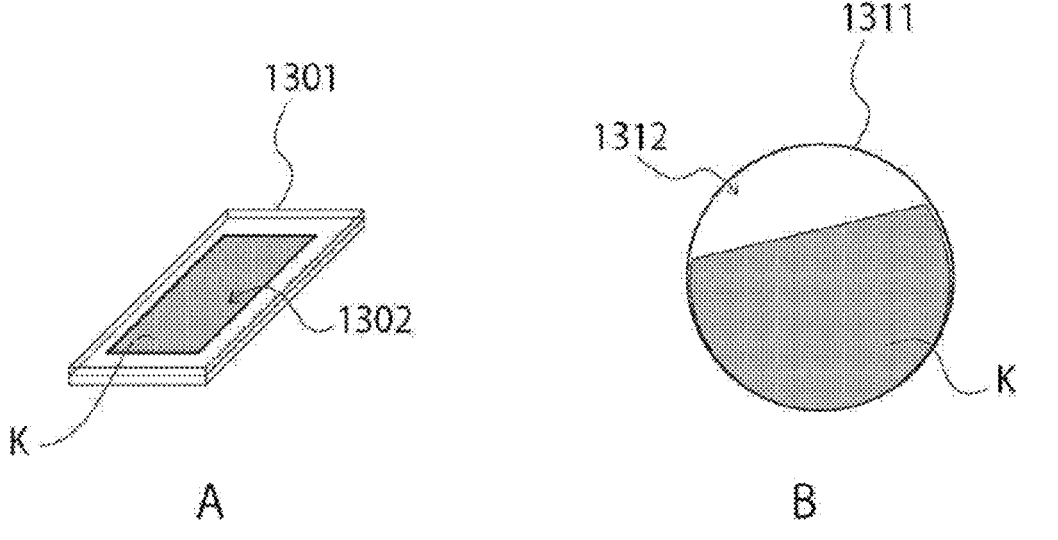
FIG. 28 is a schematic diagram illustrating a configuration example of a perfume storage unit according to a thirteenth embodiment of the present technology.

Next, a configuration example of a perfume storage unit according to a thirteenth embodiment of the present technology will be described with reference to FIG. 28. FIGS. 28A and 28B are schematic diagrams illustrating a configuration example of the perfume storage unit according to the present embodiment.

As illustrated in FIG. 28A, a perfume storage unit 1301 according to the present embodiment is formed in a plate shape and has a storage space 1302 for storing perfume K therein. Furthermore, as illustrated in FIG. 28B, the perfume storage unit 1311 according to the present embodiment is formed in a spherical shape and has a storage space 1312 for storing the perfume K therein. The perfume storage unit 1301 and the storage space 1302 can be used in the perfume cartridge according to the present technology. Note that the shape of the perfume storage unit according to the present technology is not limited to these shapes, and various shapes such as a prism can be used.

Note that the present technology can have the following configurations.

(1)

A perfume retaining member including:

a housing that includes an internal space, a first opening and a second opening that open the internal space to an outside, and a movable portion that is movable to open and close at least one of the first opening or the second opening;

a perfume storage unit that stores perfume in a sealed manner;

a perfume releasing mechanism that releases the perfume from the perfume storage unit; and a perfume retainer in which the perfume released from the perfume storage unit impregnates to be retained, in which the movable portion seals the first opening and/or the second opening in a fixed time, and opens the first opening and/or the second opening when the internal space is opened.

(2)

The perfume retaining member according to (1), in which the perfume storage unit has a shape extending in a movable direction of the movable portion.

(3)

The perfume retaining member according to (1) or (2), in which the perfume storage unit has a tubular shape.

(4)

The perfume retaining member according to any one of (1) to (3), in which a material of the perfume storage unit is glass or metal.

27

(5)

The perfume retaining member according to any one of (1) to (4), in which the perfume storage unit is arranged adjacent to the perfume retainer.

(6)

The perfume retaining member according to any one of (1) to (5), in which the perfume storage unit is arranged in the movable portion.

(7)

The perfume retaining member according to any one of (1) to (6), in which an opening is provided at an upper end and/or a lower end of the perfume storage unit, and the opening is closed by a sheet.

(8)

The perfume retaining member according to any one of (4) to (7), further including a first rotating body and a second rotating body inside the housing, the first rotating body and the second rotating body being connected to one end and another end of the perfume storage unit, respectively.

(9)

The perfume retaining member according to any one of (1) to (8), in which the perfume releasing mechanism has a protrusion that pierces the perfume storage unit.

(10)

The perfume retaining member according to (9), in which the protrusion is arranged at a position which the protrusion pierces an end portion or a side surface portion of the perfume storage unit.

(11)

The perfume retaining member according to any one of (1) to (10), in which the perfume releasing mechanism is a mechanism that splits or folds the perfume storage unit.

(12)

The perfume retaining member according to (11), in which the housing includes a main body portion having the internal space and a lid portion connected to the main body portion in a screwed manner, one end of the perfume storage unit is fixed to the internal space, and the perfume releasing mechanism is a contact portion formed inside the lid portion, and when the lid portion is screwed into the main body portion, the contact portion comes into contact with another end of the perfume storage unit to split or fold the perfume storage unit.

(13)

The perfume retaining member according to any one of (1) to (12), further including a protective member that covers a periphery of the perfume storage unit.

(14)

The perfume retaining member according to (13), in which the protective member includes an elastic body.

(15)

The perfume retaining member according to (13), in which a perfume absorption unit that absorbs the perfume released from the perfume storage unit to promote transition to the perfume retainer is provided between the protective member and the perfume storage unit.

(16)

The perfume retaining member according to (15), in which the perfume absorption unit covers a periphery of the perfume storage unit.

28

(17)

The perfume retaining member according to any one of (13) to (16), in which a portion of the perfume storage unit located near the perfume retainer is exposed from the protective member.

(18)

A scent providing device including:

a perfume retaining member including a housing that includes an internal space, a first opening and a second opening that open the internal space to an outside, and a movable portion that is movable to open and close at least one of the first opening or the second opening, a perfume storage unit that stores perfume in a sealed manner, a perfume releasing mechanism that releases the perfume from the perfume storage unit, and a perfume retainer in which the perfume released from the perfume storage unit impregnates to be retained; and a drive mechanism portion that is connected to the movable portion and drives the movable portion, in which the movable portion seals the first opening and/or the second opening in a fixed time, and opens the first opening and/or the second opening when the internal space is opened.

REFERENCE SIGNS LIST

100, 200, 300, 400, 500, 900 Scent providing device
101, 201, 301, 401, 501, 601, 701, 801, 901 Perfume cartridge (perfume retaining member)
102, 902 Discharge hole
110, 210, 911, 1012 Connection unit
111, 310, 410, 510, 912 Housing
112, 212 Threaded portion
113, 213, 313, 323, 413, 423, 513, 523, 813, 916, 932 Shaft
114, 214, 314, 414, 514, 814, 917, 933 Spring
115, 215 Perfume retainer
116, 216, 302, 316, 402, 416, 502, 516, 915, 931 Sealing valve
117, 217 First opening
118 Second opening
119, 219, 919, 934 O-ring
120, 130, 140, 220, 320, 420, 520, 620, 720, 820, 920 Perfume storage unit (ampule cartridge)
121 Heat-shrinkable tube
122, 622 Glass pipe
123 Exposed portion
124, 231, 331, 431, 831 Perfume releasing mechanism
131, 141, 623 Perfume absorption unit
221 Main body portion
222 Groove portion
223, 702, 703 Sealing sheet
602, 603 Rotating body
612, 613 Fixing groove
621, 821 Plastic case
624, 721, 722 Opening
802 Fixing base
910, 1010 Lid
913 Housing distal end portion
914, 1013 Pin
918 Impregnating material
921 Perfume storage unit fixing portion
935 Opening pin
940, 1021 Drive mechanism portion
1000 Scent providing unit
1011 Fixing unit 1020 Drive mechanism unit
R1 Internal space
SMA Shape memory alloy
D1 Movable direction

The invention claimed is:

1. A perfume retaining member comprising:
a housing that includes an internal space, a first opening and a second opening that open the internal space to an outside, and a movable portion that is movable to open and close at least one of the first opening and the second opening, wherein
the moveable portion comprises a first shaft and at least one spring axially arranged along a length of the first shaft, winding around a periphery of the first shaft and
the at least one spring biases a first sealing valve in a direction of sealing at least one of the first opening and the second opening;
a perfume storage unit that stores perfume in a sealed manner;
a perfume releasing mechanism that releases the perfume from the perfume storage unit; and
a perfume retainer in which the perfume released from the perfume storage unit impregnates to be retained, wherein
the movable portion seals at least one of the first opening and the second opening in a fixed time, and opens at least one of the first opening and the second opening when the internal space is opened.

2. The perfume retaining member according to claim 1, wherein the perfume storage unit has a shape extending in a movable direction of the movable portion.

3. The perfume retaining member according to claim 1, wherein the perfume storage unit has a tubular shape.

4. The perfume retaining member according to claim 3, further comprising a first rotating body and a second rotating body inside the housing, the first rotating body and the second rotating body being connected to one end and another end of the perfume storage unit, respectively.

5. The perfume retaining member according to claim 1, wherein a material of the perfume storage unit is glass or metal.

6. The perfume retaining member according to claim 1, wherein a portion of the perfume storage unit is exposed so that perfume that is released from the perfume storage unit is not hindered in reaching the perfume retainer.

7. The perfume retaining member according to claim 1, wherein the perfume storage unit is arranged in the movable portion.

8. The perfume retaining member according to claim 1, wherein at least one of the first opening and the second opening is provided at at least one of an upper end and and a lower end of the perfume storage unit, and at least one of the first opening and the second opening is closed by a sheet.

9. The perfume retaining member according to claim 1, wherein the perfume releasing mechanism has a protrusion that pierces the perfume storage unit.

10. The perfume retaining member according to claim 9, wherein the protrusion is arranged at a position such that the protrusion pierces an end portion or a side surface portion of the perfume storage unit.

11. The perfume retaining member according to claim 1, wherein the perfume releasing mechanism is a mechanism that splits or folds the perfume storage unit.

12. The perfume retaining member according to claim 11, wherein
the housing includes a main body portion having the internal space and a lid portion connected to the main body portion in a screwed manner,
one end of the perfume storage unit is fixed to the internal space, and the perfume releasing mechanism is a contact portion formed inside the lid portion, and
when the lid portion is screwed into the main body portion, the contact portion comes into contact with another end of the perfume storage unit to split or fold the perfume storage unit.

13. The perfume retaining member according to claim 1, further comprising a protective member that covers a periphery of the perfume storage unit.

14. The perfume retaining member according to claim 13, wherein the protective member includes an elastic body.

15. The perfume retaining member according to claim 13, wherein a perfume absorption unit that absorbs the perfume released from the perfume storage unit to promote transition to the perfume retainer is provided between the protective member and the perfume storage unit.

16. The perfume retaining member according to claim 15, wherein the perfume absorption unit covers a periphery of the perfume storage unit.

17. The perfume retaining member according to claim 13, wherein a portion of the perfume storage unit is exposed from the protective member.

18. A scent providing device comprising:
a perfume retaining member including
a housing that includes an internal space, a first opening and a second opening that open the internal space to an outside, and a movable portion that is movable to open and close at least one of the first opening and the second opening, wherein
the moveable portion comprises a first shaft and at least one spring axially arranged along a length of the first shaft, winding around a periphery of the first shaft and
the at least one spring biases a first sealing valve in a direction of sealing at least one of the first opening and the second opening,
a perfume storage unit that stores perfume in a sealed manner,
a perfume releasing mechanism that releases the perfume from the perfume storage unit, and
a perfume retainer in which the perfume released from the perfume storage unit impregnates to be retained; and
a drive mechanism portion that is connected to the movable portion and drives the movable portion, wherein
the movable portion seals at least one of the first opening and the second opening in a fixed time, and opens at least one of the first opening and the second opening when the internal space is opened.

* * * * *